United States Patent
Laughner et al.

(10) Patent No.: US 9,532,725 B2
(45) Date of Patent: Jan. 3, 2017

(54) MEDICAL DEVICES FOR MAPPING CARDIAC TISSUE

(71) Applicant: BOSTON SCIENTIFIC SCIMED, INC., Maple Grove, MN (US)

(72) Inventors: Jacob I. Laughner, St. Paul, MN (US); Shibaji Shome, Arden Hills, MN (US); Scott A. Meyer, Lakeville, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 14/632,687

(22) Filed: Feb. 26, 2015

(65) Prior Publication Data

US 2015/0250399 A1 Sep. 10, 2015

Related U.S. Application Data

(60) Provisional application No. 61/949,625, filed on Mar. 7, 2014.

(51) Int. Cl.
*A61B 5/04* (2006.01)
*A61B 5/042* (2006.01)
(Continued)

(52) U.S. Cl.
CPC ............ *A61B 5/0422* (2013.01); *A61B 5/044* (2013.01); *A61B 5/04012* (2013.01); *A61B 5/0452* (2013.01); *A61B 5/6859* (2013.01)

(58) Field of Classification Search
CPC ... A61B 5/0422; A61B 5/04012; A61B 5/044; A61B 5/6858; A61B 5/6852; G06T 17/205; G06T 2210/36
(Continued)

(56) References Cited

U.S. PATENT DOCUMENTS 4,433,380 A 2/1984 Abele et al.
4,690,152 A 9/1987 Juncosa
(Continued)

FOREIGN PATENT DOCUMENTS

EP 1190671 A2 3/2002
EP 2258263 B1 8/2012
(Continued)

OTHER PUBLICATIONS

Blanchard, Susan M., et al., "Four Algorithms for Activation Detection from Unipolar Epicardial Electrograms", IEEE Transactions on Biomedical Engineering, 36(2):256-261, Feb. 1, 1989.
(Continued)

*Primary Examiner* — Robert N Wieland
(74) *Attorney, Agent, or Firm* — Faegre Baker Daniels LLP

(57) ABSTRACT

Medical devices and methods for making and using medical devices are disclosed. An example medical device may include a catheter shaft with a plurality of electrodes coupled thereto and a processor coupled to the catheter shaft. The processor may be capable of collecting a set of signals from the plurality of electrodes and generating a data set from at least one of the set of signals. The data set may include at least one known data point and one or more unknown data points. The processor may also be capable of interpolating at least one of the unknown data points by conditioning the data set, assigning an interpolated value to at least one of the unknown data points, and assigning a confidence level to the interpolated value.

19 Claims, 10 Drawing Sheets

(51) Int. Cl.
*A61B 5/044* (2006.01)
*A61B 5/0452* (2006.01)
*A61B 5/00* (2006.01)

(58) Field of Classification Search
USPC ........................................................ 600/523
See application file for complete search history.

(56) References Cited

U.S. PATENT DOCUMENTS

| | | | |
|---|---|---|---|
| 5,254,088 A | 10/1993 | Lundquist et al. | |
| 5,383,874 A | 1/1995 | Jackson et al. | |
| 5,485,849 A | 1/1996 | Panescu et al. | |
| 5,487,391 A | 1/1996 | Panescu | |
| 5,494,042 A | 2/1996 | Panescu et al. | |
| 5,527,292 A | 6/1996 | Adams et al. | |
| 5,546,940 A | 8/1996 | Panescu et al. | |
| 5,577,509 A | 11/1996 | Panescu et al. | |
| 5,582,609 A | 12/1996 | Swanson et al. | |
| 5,595,183 A | 1/1997 | Swanson et al. | |
| 5,598,848 A | 2/1997 | Swanson et al. | |
| 5,601,088 A | 2/1997 | Swanson et al. | |
| 5,605,157 A | 2/1997 | Panescu et al. | |
| 5,609,157 A | 3/1997 | Panescu et al. | |
| 5,630,425 A | 5/1997 | Panescu et al. | |
| 5,647,870 A | 7/1997 | Kordis et al. | |
| 5,657,755 A | 8/1997 | Desai | |
| 5,687,737 A | 11/1997 | Branham et al. | |
| 5,688,267 A | 11/1997 | Panescu et al. | |
| 5,702,386 A | 12/1997 | Stern et al. | |
| 5,711,305 A | 1/1998 | Swanson et al. | |
| 5,722,402 A * | 3/1998 | Swanson .............. | A61B 5/0422 600/374 |
| 5,722,403 A | 3/1998 | McGee et al. | |
| 5,722,416 A | 3/1998 | Swanson et al. | |
| 5,732,698 A | 3/1998 | Swanson et al. | |
| 5,735,846 A | 4/1998 | Panescu et al. | |
| 5,740,808 A | 4/1998 | Panescu et al. | |
| 5,752,518 A | 5/1998 | McGee et al. | |
| 5,755,715 A | 5/1998 | Stern et al. | |
| 5,769,847 A | 6/1998 | Panescu et al. | |
| 5,792,064 A | 8/1998 | Panescu et al. | |
| 5,795,303 A | 8/1998 | Swanson et al. | |
| 5,797,903 A | 8/1998 | Swanson et al. | |
| 5,797,905 A | 8/1998 | Fleischman et al. | |
| 5,810,802 A | 9/1998 | Panescu et al. | |
| 5,830,213 A | 11/1998 | Panescu et al. | |
| 5,833,621 A | 11/1998 | Panescu et al. | |
| 5,836,874 A | 11/1998 | Swanson et al. | |
| 5,840,076 A | 11/1998 | Swanson et al. | |
| 5,846,238 A | 12/1998 | Jackson et al. | |
| 5,846,239 A | 12/1998 | Swanson et al. | |
| 5,848,969 A | 12/1998 | Panescu et al. | |
| 5,853,409 A | 12/1998 | Swanson et al. | |
| 5,853,411 A | 12/1998 | Whayne et al. | |
| 5,868,680 A | 2/1999 | Steiner et al. | |
| 5,868,736 A | 2/1999 | Swanson et al. | |
| 5,871,483 A | 2/1999 | Jackson et al. | |
| 5,876,336 A | 3/1999 | Swanson et al. | |
| 5,879,348 A | 3/1999 | Owens et al. | |
| 5,891,136 A | 4/1999 | McGee et al. | |
| 5,904,651 A | 5/1999 | Swanson et al. | |
| 5,904,680 A | 5/1999 | Kordis et al. | |
| 5,906,614 A | 5/1999 | Stern et al. | |
| 5,908,445 A | 6/1999 | Whayne et al. | |
| 5,911,739 A | 6/1999 | Kordis et al. | |
| 5,916,163 A | 6/1999 | Panescu et al. | |
| 5,925,038 A | 7/1999 | Panescu et al. | |
| 5,928,228 A | 7/1999 | Kordis et al. | |
| 5,935,079 A | 8/1999 | Swanson et al. | |
| 5,941,251 A | 8/1999 | Panescu et al. | |
| 5,954,661 A | 9/1999 | Greenspon et al. | |
| 5,954,662 A | 9/1999 | Swanson et al. | |
| 5,961,513 A | 10/1999 | Swanson et al. | |
| 5,968,040 A | 10/1999 | Swanson et al. | |
| 6,014,581 A | 1/2000 | Whayne et al. | |
| 6,014,590 A | 1/2000 | Whayne et al. | |
| 6,022,346 A | 2/2000 | Panescu et al. | |
| 6,030,379 A | 2/2000 | Panescu et al. | |
| 6,030,382 A | 2/2000 | Fleischman et al. | |
| 6,035,226 A | 3/2000 | Panescu | |
| 6,047,218 A | 4/2000 | Whayne et al. | |
| 6,049,732 A | 4/2000 | Panescu et al. | |
| 6,053,912 A | 4/2000 | Panescu et al. | |
| 6,056,745 A | 5/2000 | Panescu et al. | |
| 6,070,094 A | 5/2000 | Swanson et al. | |
| 6,071,278 A | 6/2000 | Panescu et al. | |
| 6,076,012 A | 6/2000 | Swanson et al. | |
| 6,086,532 A | 7/2000 | Panescu et al. | |
| 6,095,150 A | 8/2000 | Panescu et al. | |
| 6,101,409 A | 8/2000 | Swanson et al. | |
| 6,101,410 A | 8/2000 | Panescu et al. | |
| 6,106,460 A | 8/2000 | Panescu et al. | |
| 6,106,522 A | 8/2000 | Fleischman et al. | |
| 6,113,591 A | 9/2000 | Whayne et al. | |
| 6,115,626 A | 9/2000 | Whayne et al. | |
| 6,123,702 A | 9/2000 | Swanson et al. | |
| 6,129,669 A | 10/2000 | Panescu et al. | |
| 6,129,724 A | 10/2000 | Fleischman et al. | |
| 6,162,184 A | 12/2000 | Swanson et al. | |
| 6,165,169 A | 12/2000 | Panescu et al. | |
| 6,171,306 B1 | 1/2001 | Swanson et al. | |
| 6,179,835 B1 | 1/2001 | Panescu et al. | |
| 6,183,468 B1 | 2/2001 | Swanson et al. | |
| 6,188,924 B1 | 2/2001 | Swanson et al. | |
| 6,192,266 B1 | 2/2001 | Dupree et al. | |
| 6,197,021 B1 | 3/2001 | Panescu et al. | |
| 6,206,831 B1 | 3/2001 | Suorsa et al. | |
| 6,216,043 B1 | 4/2001 | Swanson et al. | |
| 6,221,013 B1 | 4/2001 | Panescu et al. | |
| 6,226,542 B1 | 5/2001 | Reisfeld | |
| 6,233,491 B1 | 5/2001 | Kordis et al. | |
| 6,245,061 B1 | 6/2001 | Panescu et al. | |
| 6,245,065 B1 | 6/2001 | Panescu et al. | |
| 6,256,540 B1 | 7/2001 | Panescu et al. | |
| 6,289,239 B1 | 9/2001 | Panescu et al. | |
| 6,293,943 B1 | 9/2001 | Panescu et al. | |
| 6,301,496 B1 | 10/2001 | Reisfeld | |
| 6,330,473 B1 | 12/2001 | Swanson et al. | |
| 6,353,751 B1 | 3/2002 | Swanson et al. | |
| 6,370,435 B2 | 4/2002 | Panescu et al. | |
| 6,389,311 B1 | 5/2002 | Whayne et al. | |
| 6,391,024 B1 | 5/2002 | Sun et al. | |
| 6,428,536 B2 | 8/2002 | Panescu et al. | |
| 6,456,864 B1 | 9/2002 | Swanson et al. | |
| 6,456,867 B2 | 9/2002 | Reisfeld | |
| 6,471,699 B1 | 10/2002 | Fleischman et al. | |
| 6,487,441 B1 | 11/2002 | Swanson et al. | |
| 6,488,679 B1 | 12/2002 | Swanson et al. | |
| 6,490,468 B2 | 12/2002 | Panescu et al. | |
| 6,494,880 B1 | 12/2002 | Swanson et al. | |
| 6,500,172 B1 | 12/2002 | Panescu et al. | |
| 6,508,765 B2 | 1/2003 | Suorsa et al. | |
| 6,516,807 B1 | 2/2003 | Panescu et al. | |
| 6,522,913 B2 | 2/2003 | Swanson et al. | |
| 6,542,773 B2 | 4/2003 | Dupree et al. | |
| 6,556,695 B1 | 4/2003 | Packer et al. | |
| 6,565,511 B2 | 5/2003 | Panescu et al. | |
| 6,569,160 B1 | 5/2003 | Goldin et al. | |
| 6,597,955 B2 | 7/2003 | Panescu et al. | |
| 6,615,073 B1 | 9/2003 | Panescu et al. | |
| 6,625,482 B1 | 9/2003 | Panescu et al. | |
| 6,647,281 B2 | 11/2003 | Morency | |
| 6,652,513 B2 | 11/2003 | Panescu et al. | |
| 6,658,279 B2 | 12/2003 | Swanson et al. | |
| 6,668,198 B2 | 12/2003 | Swanson et al. | |
| 6,735,465 B2 | 5/2004 | Panescu | |
| 6,736,811 B2 | 5/2004 | Panescu et al. | |
| 6,745,076 B2 | 6/2004 | Wohlgemuth et al. | |
| 6,746,401 B2 | 6/2004 | Panescu | |
| 6,788,969 B2 | 9/2004 | Dupree et al. | |
| 6,790,206 B2 | 9/2004 | Panescu | |
| 6,824,515 B2 | 11/2004 | Suorsa et al. | |
| 6,895,267 B2 | 5/2005 | Panescu et al. | |
| 7,194,294 B2 | 3/2007 | Panescu et al. | |

(56) References Cited

U.S. PATENT DOCUMENTS

| | | | |
|---|---|---|---|
| 7,364,546 B2 | 4/2008 | Panescu et al. |
| 7,505,810 B2 | 3/2009 | Harlev et al. |
| 7,515,954 B2 | 4/2009 | Harlev et al. |
| 7,565,208 B2 | 7/2009 | Harris et al. |
| 7,582,084 B2 | 9/2009 | Swanson et al. |
| 7,676,264 B1 | 3/2010 | Pillai et al. |
| 7,699,829 B2 | 4/2010 | Harris et al. |
| 7,729,752 B2 | 6/2010 | Harlev et al. |
| 7,774,051 B2 | 8/2010 | Voth |
| 7,794,404 B1 | 9/2010 | Gutfinger et al. |
| 7,869,854 B2 | 1/2011 | Shachar et al. |
| 7,925,349 B1 | 4/2011 | Wong et al. |
| 7,930,018 B2 | 4/2011 | Harlev et al. |
| 7,937,136 B2 | 5/2011 | Harlev et al. |
| 7,945,326 B1 | 5/2011 | Wong et al. |
| 7,946,995 B1 | 5/2011 | Koh et al. |
| 7,953,475 B2 | 5/2011 | Harlev et al. |
| 7,957,791 B2 | 6/2011 | Harlev et al. |
| 7,957,792 B2 | 6/2011 | Harlev et al. |
| 7,957,813 B1 | 6/2011 | Persson et al. |
| 8,010,196 B1 | 8/2011 | Wong et al. |
| 8,019,419 B1 | 9/2011 | Panescu et al. |
| 8,032,218 B2 | 10/2011 | Wong et al. |
| 8,038,625 B2 | 10/2011 | Afonso et al. |
| 8,065,005 B1 | 11/2011 | Wong et al. |
| 8,103,327 B2 | 1/2012 | Harlev et al. |
| 8,103,338 B2 | 1/2012 | Harlev et al. |
| 8,128,617 B2 | 3/2012 | Bencini et al. |
| 8,137,343 B2 | 3/2012 | Harlev et al. |
| 8,165,666 B1 | 4/2012 | Briggs et al. |
| 8,167,876 B2 | 5/2012 | Harlev et al. |
| 8,175,680 B2 | 5/2012 | Panescu |
| 8,202,224 B2 | 6/2012 | Gutfinger et al. |
| 8,208,999 B2 | 6/2012 | Wenzel et al. |
| 8,280,511 B2 | 10/2012 | Zhao et al. |
| 8,306,623 B2 | 11/2012 | Wong et al. |
| 8,364,253 B2 | 1/2013 | Voth |
| 8,369,922 B2 | 2/2013 | Paul et al. |
| 8,386,049 B2 | 2/2013 | Persson et al. |
| 8,406,866 B2 | 3/2013 | Deno et al. |
| 8,414,579 B2 | 4/2013 | Kim et al. |
| 8,449,535 B2 | 5/2013 | Deno et al. |
| 8,504,152 B2 | 8/2013 | Wenzel et al. |
| 8,504,153 B2 | 8/2013 | Wenzel et al. |
| 8,554,333 B2 | 10/2013 | Wu et al. |
| 8,571,647 B2 | 10/2013 | Harlev et al. |
| 8,600,497 B1 | 12/2013 | Yang et al. |
| 8,712,519 B1 | 4/2014 | Panescu et al. |
| 8,830,235 B1 * | 9/2014 | Guskov | G06T 17/205 345/420 |
| 2001/0000791 A1 | 5/2001 | Suorsa et al. |
| 2001/0009976 A1 | 7/2001 | Panescu et al. |
| 2001/0018608 A1 | 8/2001 | Panescu et al. |
| 2001/0020126 A1 | 9/2001 | Swanson et al. |
| 2001/0025175 A1 | 9/2001 | Panescu et al. |
| 2001/0044585 A1 | 11/2001 | Dupree et al. |
| 2002/0058870 A1 | 5/2002 | Panescu et al. |
| 2002/0065465 A1 | 5/2002 | Panescu et al. |
| 2002/0099415 A1 | 7/2002 | Panescu et al. |
| 2002/0111548 A1 | 8/2002 | Swanson et al. |
| 2002/0115941 A1 | 8/2002 | Whayne et al. |
| 2002/0143250 A1 | 10/2002 | Panescu et al. |
| 2002/0161422 A1 | 10/2002 | Swanson et al. |
| 2002/0193790 A1 | 12/2002 | Fleischman et al. |
| 2002/0198520 A1 | 12/2002 | Coen et al. |
| 2003/0028118 A1 | 2/2003 | Dupree et al. |
| 2003/0055419 A1 | 3/2003 | Panescu et al. |
| 2003/0065322 A1 | 4/2003 | Panescu et al. |
| 2003/0078494 A1 | 4/2003 | Panescu et al. |
| 2003/0078509 A1 | 4/2003 | Panescu |
| 2003/0088244 A1 | 5/2003 | Swanson et al. |
| 2003/0093067 A1 | 5/2003 | Panescu |
| 2003/0093069 A1 | 5/2003 | Panescu et al. |
| 2003/0144655 A1 | 7/2003 | Panescu |
| 2003/0153907 A1 | 8/2003 | Suorsa et al. |
| 2003/0158477 A1 | 8/2003 | Panescu |
| 2003/0199863 A1 | 10/2003 | Swanson et al. |
| 2003/0208123 A1 | 11/2003 | Panescu |
| 2004/0015065 A1 | 1/2004 | Panescu et al. |
| 2004/0097803 A1 | 5/2004 | Panescu |
| 2004/0254437 A1 | 12/2004 | Hauck et al. |
| 2005/0177151 A1 | 8/2005 | Coen et al. |
| 2005/0197657 A1 | 9/2005 | Goth et al. |
| 2005/0215945 A1 | 9/2005 | Harris et al. |
| 2005/0245949 A1 | 11/2005 | Goth et al. |
| 2006/0030833 A1 | 2/2006 | Harris et al. |
| 2006/0064083 A1 | 3/2006 | Khalaj et al. |
| 2006/0089688 A1 | 4/2006 | Panescu |
| 2006/0135957 A1 | 6/2006 | Panescu |
| 2006/0184166 A1 | 8/2006 | Valle et al. |
| 2007/0055227 A1 | 3/2007 | Khalaj et al. |
| 2007/0073179 A1 | 3/2007 | Afonso et al. |
| 2007/0073286 A1 | 3/2007 | Panescu et al. |
| 2007/0156048 A1 | 7/2007 | Panescu et al. |
| 2007/0232949 A1 | 10/2007 | Saksena |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0190438 A1 | 8/2008 | Harlev et al. |
| 2008/0249424 A1 | 10/2008 | Harlev et al. |
| 2008/0262361 A1 | 10/2008 | Gutfinger et al. |
| 2009/0018597 A1 | 1/2009 | Wenzel et al. |
| 2009/0171274 A1 | 7/2009 | Harlev et al. |
| 2009/0171345 A1 | 7/2009 | Miller et al. |
| 2009/0177071 A1 | 7/2009 | Harlev et al. |
| 2009/0253976 A1 | 10/2009 | Harlev et al. |
| 2009/0262109 A1 | 10/2009 | Markowitz et al. |
| 2009/0281439 A1 | 11/2009 | Harlev et al. |
| 2009/0287267 A1 | 11/2009 | Wenzel et al. |
| 2009/0299211 A1 | 12/2009 | Wenzel et al. |
| 2010/0004712 A1 | 1/2010 | Zhao et al. |
| 2010/0023085 A1 | 1/2010 | Wu et al. |
| 2010/0030294 A1 | 2/2010 | Wong et al. |
| 2010/0091834 A1 | 4/2010 | Cheung et al. |
| 2010/0094274 A1 | 4/2010 | Narayan et al. |
| 2010/0106009 A1 | 4/2010 | Harlev et al. |
| 2010/0106154 A1 | 4/2010 | Harlev et al. |
| 2010/0274150 A1 | 10/2010 | Harlev et al. |
| 2010/0286550 A1 | 11/2010 | Harlev et al. |
| 2010/0286551 A1 | 11/2010 | Harlev et al. |
| 2010/0305433 A1 | 12/2010 | Harlev et al. |
| 2010/0324414 A1 | 12/2010 | Harlev et al. |
| 2011/0028821 A1 | 2/2011 | Bojovic et al. |
| 2011/0105928 A1 | 5/2011 | Bojovic et al. |
| 2011/0112413 A1 | 5/2011 | Panescu et al. |
| 2011/0112414 A1 | 5/2011 | Panescu et al. |
| 2011/0112415 A1 | 5/2011 | Bojovic et al. |
| 2011/0125150 A1 | 5/2011 | Deno et al. |
| 2011/0160574 A1 | 6/2011 | Harlev et al. |
| 2011/0166472 A1 | 7/2011 | Björling et al. |
| 2011/0184300 A1 | 7/2011 | Shvilkin et al. |
| 2011/0190625 A1 | 8/2011 | Harlev et al. |
| 2011/0202113 A1 | 8/2011 | Persson et al. |
| 2011/0275949 A1 | 11/2011 | Harlev et al. |
| 2011/0282186 A1 | 11/2011 | Harlev et al. |
| 2011/0282187 A1 | 11/2011 | Harlev et al. |
| 2011/0306896 A1 | 12/2011 | Altmann |
| 2012/0004533 A1 * | 1/2012 | Peng | A61B 6/12 600/424 |
| 2012/0053470 A1 | 3/2012 | Wong et al. |
| 2012/0078077 A1 | 3/2012 | Harlev et al. |
| 2012/0130267 A1 | 5/2012 | Harlev et al. |
| 2012/0143030 A1 | 6/2012 | Harlev et al. |
| 2012/0151301 A1 | 6/2012 | Izumi et al. |
| 2012/0184858 A1 | 7/2012 | Harlev et al. |
| 2012/0184863 A1 | 7/2012 | Harlev et al. |
| 2012/0184864 A1 | 7/2012 | Harlev et al. |
| 2012/0184865 A1 | 7/2012 | Harlev et al. |
| 2012/0245481 A1 | 9/2012 | Blanco et al. |
| 2012/0253161 A1 | 10/2012 | Harlev et al. |
| 2012/0265054 A1 | 10/2012 | Olson |
| 2012/0277574 A1 | 11/2012 | Panescu |
| 2012/0283587 A1 | 11/2012 | Gosh et al. |
| 2013/0035576 A1 | 2/2013 | O'Grady et al. |

(56) References Cited

U.S. PATENT DOCUMENTS

| | | | |
|---|---|---|---|
| 2013/0060245 | A1 | 3/2013 | Grunewald et al. |
| 2013/0096447 | A1 | 4/2013 | Dhawan et al. |
| 2013/0123775 | A1 | 5/2013 | Grunewald et al. |
| 2013/0137999 | A1 | 5/2013 | Wenzel et al. |
| 2013/0138003 | A1 | 5/2013 | Kaski |
| 2013/0173222 | A1 | 7/2013 | Voth |
| 2013/0204124 | A1 | 8/2013 | Duindam et al. |
| 2013/0226016 | A1 | 8/2013 | Narayan et al. |
| 2013/0274582 | A1 | 10/2013 | Afonso et al. |
| 2013/0303892 | A1 | 11/2013 | Zhao et al. |
| 2013/0303945 | A1 | 11/2013 | Blumenkranz et al. |
| 2014/0100440 | A1 | 4/2014 | Cheline et al. |
| 2014/0278321 | A1 | 9/2014 | Zhang et al. |
| 2014/0310016 | A1 | 10/2014 | Kenney et al. |
| 2015/0016749 | A1 | 1/2015 | Chen et al. |
| 2015/0065836 | A1 | 3/2015 | Thakur et al. |
| 2015/0196214 | A1 | 7/2015 | Shuros et al. |
| 2015/0196215 | A1 | 7/2015 | Laughner et al. |
| 2015/0257671 | A1 | 9/2015 | Laughner et al. |

FOREIGN PATENT DOCUMENTS

| | | | |
|---|---|---|---|
| WO | 2007035306 | A2 | 3/2007 |
| WO | 2007137045 | A2 | 11/2007 |
| WO | 2007146864 | A3 | 12/2007 |
| WO | 2008097767 | A2 | 8/2008 |
| WO | 2009085108 | A1 | 7/2009 |
| WO | 2009123819 | A2 | 10/2009 |
| WO | 2010051183 | A1 | 5/2010 |
| WO | 2010058372 | A1 | 5/2010 |
| WO | 2010123637 | A2 | 10/2010 |
| WO | 2010129095 | A2 | 11/2010 |
| WO | 2011021948 | A1 | 2/2011 |
| WO | 2011142931 | A1 | 11/2011 |
| WO | 20111142932 | A1 | 11/2011 |
| WO | 2012092016 | A1 | 7/2012 |
| WO | 2012097059 | A1 | 7/2012 |
| WO | 2012097067 | A1 | 7/2012 |
| WO | WO2012151301 | A1 | 11/2012 |
| WO | 2015066322 | A1 | 5/2015 |
| WO | 2015106196 | A1 | 7/2015 |
| WO | 2015106201 | A1 | 7/2015 |
| WO | 2015106254 | A | 7/2015 |
| WO | 2015134276 | A1 | 9/2015 |

OTHER PUBLICATIONS

Blanchard, Susan M., et al., "Interpolating Unipolar Epicardial Potentials from Electrodes Separated by Increasing Distances", PACE and Clinical Electrophysiology, 12(12):1938-1955, Dec. 1, 1989.

Chen I-Ching, et al. "Radioteguency Ablation Therapy in Concealed Left Free Wall Accessory Pathway With Decremental Conduction," The Cardiopulmonary and Critical Care Journal. CHEST. New York City, New York. pp. 107(1 ):40-45, Jan. 1995.

Corinna B. Brunckorst, et al. "Identification of the Ventricular Tachycardia Isthmus After Infarction by Pace Mapping," Circulation Journal of the American Heart Assoication. Volume Circulation, American Heart Association. Dallas, Texas, 110:652-659, Aug. 2, 2004.

Deepak Bhakta et al. "Principles of Electroanatomic Mapping," Indian Pacing and Electrophysiology Journal. Krannert Institute of Cardiology. Indianapolis, Indiana, 8(1 ):32-50, 2008.

Etienne M. Aliot, et al. "EHRA/HRS Expert Consensus on Catheter Ablation of Ventricular Arrhythmias," European Society of Cardiology. The European Heart Rhythm Association, 11:771-817, 2009.

Faes, L., et. al. Principal Component Analysis and Cluster Analysis for Measuring the Local Organization of Human Atrial Fibrillation. Med. Biol. Eng. Comput., 39(6): 656-663, 2001.

Feifan Ouyang, et al, "Electroanatomic Substrate of Idiopathic Left Ventricular Tachycardia: Unidirectional Block and Macroreentry Within the Purkinje Network," Circulation Journal of the American Heart Association. American Heart Association. Dallas, Texas. 105(10):462-469, 2002.

He; Ye H., "An interactive graphical system for automated mapping and display of cardiac rhythms", Journal of Electrocardiology, vol. 32, No. 3, Jul. 1, 1999, pp. 225-241.

Hong Cao, et al. "FEM Analysis of Predicting Electrode-Myocardium Contact From RF Cardiac Catheter Ablation System Impedance," IEEE Transactions on Biomedical Engineering. IEEE Engineering in Medicine and Biology Society, Madison, Wisconsin. 49(6):520-526, Jun. 2002.

International Search Report and Written Opinion issued in PCT/US2014/063148, mailed Feb. 4, 2015, 11 pages.

International Search Report and Written Opinion issued in PCT/US2015/011013, mailed Sep. 4, 2015, 11 pages.

International Search Report and Written Opinion issued in PCT/US2015/011025, mailed Apr. 2, 2015, 8 pages.

International Search Report and Written Opinion issued in PCT/US2015/011170, mailed Apr. 28, 2015, 9 pages.

International Search Report and Written Opinion issued in PCT/US2015/017775, mailed May 26, 2015, 11 pages.

International Search Report and Written Opinion in PCT/US2015/018016, mailed May 20, 2015, 13 pages.

Jang-Zern Tsai, et al. "Dependence of Apparent Resistance of Four-Electrode Probes on Insertion Depth," IEEE Transactions on Biomedical Engineering. IEEE Engineering in Medicine and Biology Society, Madison, Wisconsin, 47 (1):41-48, Jan. 2000.

Jang-Zern Tsai, et al. "Error Analysis of Tissue Resistivity Measurement. IEEE Transactions on Biomedical Engineering," IEEE Engineering in Medicine and Biology Society. Madison, Wisconsin, 49(5):484-494, May 2002.

Jason NG, et al., "Understanding and Interpreting Dominant Frequency Analysis of AF Electrograms," J Cardiovasc Electrophysiol, Blackwell. Chicago, Illinois. 18(6):680-685, 2007.

Ji-Qiang Hu, et al. "The Characteristics of Veraparmil-sensitive Idiopathic left Ventricular Tachycardia combined with a left accessory pathway and the effect of radiofrequency catheter ablation," Clinical Research Electrophysiology and Ablation. The European Society of Cardiology, Beijing, China. pp. 704-708, Jun. 30, 2011.

Joseph B. Morton, et al. "Sensitivity and Specificity of Concealed Entrainment for the Identification of Critical Isthmus in the Atrium: Relationship to Rate, Anatomic Location and Antidromic Penetration," Journal of the American College of Cardiology. Elsevier Science Inc. Melbourne, Australia. 39(5):896-906. Mar. 6, 2002.

Ken Okumura, et al. "Pathophysiology and Natural History Ventricular Tachycardia. Demonstration of the Presence of Slow Conduction During Sustained Ventricular Tachycardia in Man: Use of Transient Entrainment of the Tachycardia," Department of Medicine, Case Western Reserve University/University Hospitals of Cleveland, Ohio and the University of Alabama at Birmingham, 75(2):369-378, Feb. 1987.

Koonlawee Nademanee et al. "How to perform Electrogam-guided Atrial Fibrillation Ablation," The Pacifc Rim Electrophysiology Research Institute. Heart Rhythm Society. Inglewood, California, 3(8):981-984, Aug. 2006.

Koonlawee Nademanee, et al. A New Approach for Catheter Ablation of Atrial Fibrillation: Mapping of the Electrophysiologic Substrate. Journal of the American College of Cardiology. Jun. 2, 2004, 43(11 ):2044-2053. Elsevier Inc. Inglewood, California; and Bangkok, Thailand.

Martis, R. J., et. al. A Two-Stage Mechanism for Registration and Classification of ECG Using Gaussian Mixture Model. Pattern Recognition, 42(11): 2979-2988, 2009.

Minglong Chen, et al. "Non-contact mapping and linear ablation of the left posterior fascicle during sinus rhythm in the treatment of idiopathic left ventricular tachycardia," European Society of Cardiology. vol. 7: pp. 138-144. Elsevier Ltd. China, 2005.

Nademanee K, et al. "Catheter Ablation of Atrial Fibrillation guided by complex Fractionated Atrial Electrogram Mapping of Atrial Fibrillation Substrate," Pacific Rim Eltrophysiology Research Institute. Elsevier Ltd. Los Angeles, California, 55(3):1-12, May 2010.

Prashanthan Sanders, et al. Spectral Analysis Identifies Sites of High-Frequency Activity Maintaining Atrial Fibrillation in

(56) References Cited

OTHER PUBLICATIONS

Humans. Circulation Journal of the American Heart Association. The American Heart Association, Inc. Dallas, Texas. 112:789-797, Aug. 9, 2005.

Quan Ni et al. "A Novel Interpolation Method of Electric Potential Fields in the Heart during Excitation" Annals of Biomedical Engineering. Biomedical Engineering Society. Salt Lake City, Utah. vol. 26:597-607, 1998.

Shiro Nakahara, et al. "Characterization of the Arrhythmogenic Substrate in Ischemic and Nonischemic Cardiomyopathy. Implications for Catheter Ablation of Hemodynamically Unstable Ventricular Tachycardia," Journal of the American College of Cardiology. Los Angeles, California, 55(21):2355-2365, May 25, 2010.

Stevenson WG, et al, "Identifying sites for Catheter Ablation of Ventricular Tachycardia," PubMed NCBI. MeSH Terms, Abstract, Jun. 1992.

Takeshi Tsuchiya. et al. "Significance of Late Diastolic Potential Preceding Purkinje Potential in Verapamil-Sensitive Idiopathic Left Ventricular Tachycardia." American Heart Association. Japan, pp. 2408-2413, May 11, 1999.

William G. Stevenson, et al. "Identification of Reentry Circuit Sites During Catheter Mapping and Radiofrequency Ablation of Ventricular Tachycardia Late After Myocardial Infarction," Circulation. America Heart Association. Los Angeles, California. 88(4):1646-1670, Oct. 1993.

William G. Stevenson, et al. "Recording Techniques of Clinical Electrophysiology," J Cardiovasc Electrophysiol. Blackwell. Boston, Massachusetts. 16(9):1017-1022, 2005.

William G. Stevenson, et al. Journal of the American College of Cardiology. Fractionated Endocardial Electrograms are Associated With Slow Conduction in Humans: Evidence From Pace-Mapping, Los Angeles, California, 13(2):369-376, Feb. 1989.

Yilmaz, B., et. al. Usage of Spline Interpolation in Catheter-Based Cardiac Mapping. Turk. J. Elec. Eng. & Comp. Sci., 18(6):989-1002, 2010.

International Preliminary Report on Patentability issued in PCT/US2014/063148, mailed May 12, 2016, 9 pages.

International Preliminary Report on Patentability issued in PCT/US2015/011013 mailed Jul. 28, 2016, 8 pages.

International Preliminary Report on Patentability issued in PCT/US2015/011025, mailed Jul. 28, 2016, 6 pages.

International Preliminary Report on Patentability issued in PCT/US2015/011170 mailed Jul. 28, 2016, 7 pages.

International Preliminary Report on Patentability issued in PCT/US2015/018016, mailed Sep. 22, 2016, 9 pages.

International Preliminary Report on Patentability issued in PCT/US2015/017775 mailed Sep. 22, 2016, 7 pages.

* cited by examiner

FIG. 4

MEDICAL DEVICES FOR MAPPING CARDIAC TISSUE

CROSS-REFERENCE TO RELATED APPLICATIONS

This application claims priority under 35 U.S.C. §119 to U.S. Provisional Application Ser. No. 61/949,625, filed Mar. 7, 2014, the entirety of which is incorporated herein by reference.

TECHNICAL FIELD

The present disclosure pertains to medical devices, and methods for manufacturing medical devices. More particularly, the present disclosure pertains to medical devices and methods for mapping and/or ablating cardiac tissue.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices. An example medical device is disclosed. The medical device includes a catheter shaft with a plurality of electrodes coupled thereto. A processor is coupled to the catheter shaft. The processor is capable of collecting a set of signals from the plurality of electrodes and generating a data set from at least one of the set of signals. The data set includes at least one known data point and one or more unknown data points. The processor is also capable of interpolating at least one of the unknown data points by conditioning the data set, assigning an interpolated value to at least one of the unknown data points, and assigning a confidence level to the interpolated value.

Alternatively or additionally to any of the embodiments above, collecting the set of signals includes determining an activation time at one or more of the plurality of electrodes.

Alternatively or additionally to any of the embodiments above, assigning a value to at least one of the unknown data points includes assigning an activation time to at least one of the unknown data points.

Alternatively or additionally to any of the embodiments above, determining the activation time includes identifying a fiducial point corresponding to a change in electrical potential and determining a time latency between a reference point and the fiducial point.

Alternatively or additionally to any of the embodiments above, interpolating at least one of the unknown data points by conditioning the data set includes creating a mesh of interconnected nodes between the known data points, the unknown data points, or both the known and unknown data points.

Alternatively or additionally to any of the embodiments above, interpolating at least one of the unknown data points by conditioning the data set includes upsampling the mesh of interconnected nodes.

Alternatively or additionally to any of the embodiments above, interpolating at least one of the unknown data points by conditioning the data set includes utilizing a non-linear distance between the known data points, unknown data points, or both the known and unknown data points.

Alternatively or additionally to any of the embodiments above, interpolating at least one of the unknown data points by conditioning the data set includes utilizing a geodesic distance between the known data points, unknown data points, or both the known and unknown data points.

Alternatively or additionally to any of the embodiments above, interpolating at least one of the unknown data points by conditioning the data set includes weighting the known data points and wherein weighting the known data points includes determining weighting coefficients from a weighting function.

Alternatively or additionally to any of the embodiments above, the processor is capable of generating a graphical display of at least one known data point, one or more unknown data points or both. The graphical display includes an activation map.

Alternatively or additionally to any of the embodiments above, the graphical display further comprises an interpolated activation map.

Alternatively or additionally to any of the embodiments above, the graphical display further comprises a confidence map representing the confidence level.

An example method for displaying cardiac mapping data is disclosed. The method includes storing a set of activation times on a memory. The set of activation times includes one or more known activation times and one or more unknown activation times. The method also includes outputting the set of activation times to a display unit, displaying the activation times on a first panel of the display unit, interpolating the unknown activation times, displaying the interpolated activation times on a second panel of the display unit, and displaying a confidence map on a third panel of the display unit. The confidence map displays the level of confidence for the interpolated activation times.

Alternatively or additionally to any of the embodiments above, storing a set of activation times on a memory includes identifying a fiducial point corresponding to a change in electrical potential and determining a time latency between a reference point and the fiducial point.

Alternatively or additionally to any of the embodiments above, interpolating the unknown activation times includes utilizing a non-linear distance between two electrodes of a constellation catheter.

Alternatively or additionally to any of the embodiments above, interpolating the unknown activation times includes utilizing a geodesic distance two electrodes of a constellation catheter.

Alternatively or additionally to any of the embodiments above, interpolating the unknown activation times includes weighting the known activation times and wherein weighting the known activation times includes determining weighting coefficients from a weighting function.

An example medical device is disclosed. The medical device includes a catheter shaft with a plurality of electrodes coupled thereto. A processor is coupled to the catheter shaft. The processor is capable of sensing electrical activity with the plurality of electrodes and determining activation times at the plurality of electrodes based on the sensed electrical activity. Determining activation times at the plurality of electrodes includes determining one or more known activation times and one or more unknown activation times. The processor is also capable of interpolating the one or more unknown activation times, assigning an interpolated activation time to each of the one or more unknown activation times, and assigning a confidence level to the interpolated activation times.

Alternatively or additionally to any of the embodiments above, the processor is capable of generating a graphical display. The graphical display includes an activation map, an interpolated activation map, or both.

Alternatively or additionally to any of the embodiments above, the graphical display further comprises a confidence map representing the confidence level of the interpolated activation times.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 4 is an illustration of an example activation map displaying known and unknown activation times;

Figure 1:
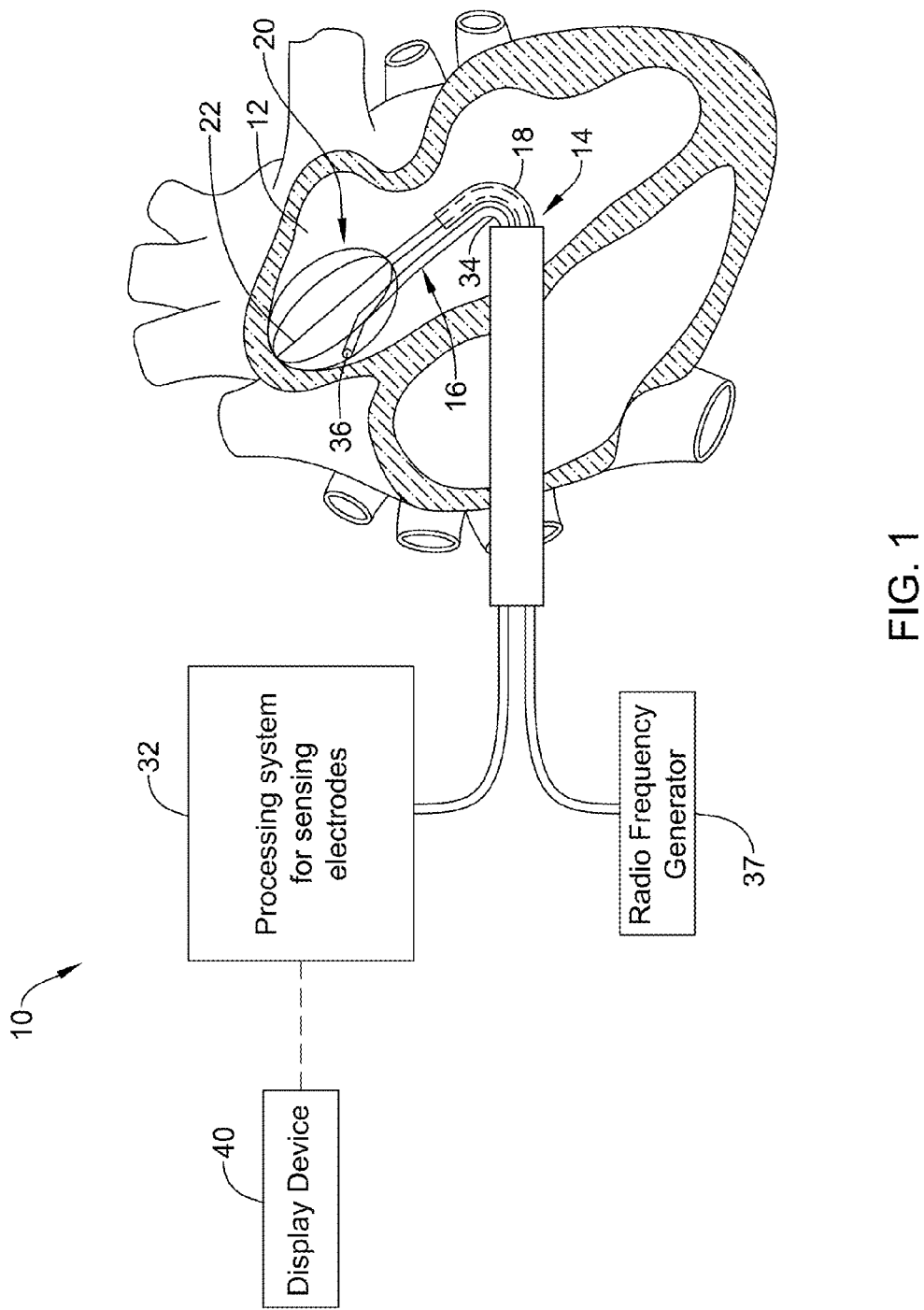
FIG. 1 is a schematic view of an example catheter system for accessing a targeted tissue region in the body for diagnostic and/or therapeutic purposes.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Mapping the electrophysiology of heart rhythm disorders often involves the introduction of a constellation catheter or other mapping/sensing device having a plurality of electrodes and/or sensors (e.g., CONSTELLATION®, commercially available from Boston Scientific) into a cardiac chamber. The sensors detect the electric activity of the heart at sensor locations. It may be desirable to have the electric activity processed into electrogram signals that accurately represent cellular excitation through cardiac tissue relative to the sensor locations. A processing system may then analyze and output the signal to a display device. Further, the processing system may output the signal as an activation or vector field map. The physician may use the activation or vector field map to perform a diagnostic procedure.

However, in some cases the sensing electrodes may fail to accurately detect the electrical activity of heart. The failure of the electrodes to detect a signal may limit the ability of the processing system to accurately display information used for diagnostic procedures. For example, an activation map may be generated that contains missing information and/or inaccurate visual representations. Therefore, it may be desirable to replace poor or non-existent electrical signal information with information that is believed to be accurate. In some instances, interpolation may be used to replace poor/missing data. Standard interpolation methods may have limitations due to both the temporal nature of the activation signals and the three-dimensional spatial configuration of sensing electrodes located in an anatomical region. The methods and systems disclosed herein are designed to overcome at least some of the limitations of standard interpolation methods used to interpolate poor or non-existent activation signals. For example, some of the methods disclosed herein may utilize geodesic distance calculations in order to improve the accuracy of interpolation methods. Other methods and medical devices are also disclosed.

FIG. 1 is a schematic view of a system 10 for accessing a target region 12 in the body for diagnostic and/or therapeutic purposes. FIG. 1 generally shows system 10 deployed in the left atrium of the heart. Alternatively, system 10 can be deployed in other regions of the heart, such as the left ventricle, right atrium, or right ventricle. While the illustrated embodiment shows system 10 being used for mapping and/or ablating myocardial tissue, system 10 (and the methods described herein) may alternatively be configured for use in other tissue mapping and/or ablation applications, such as procedures for ablating or otherwise involving tissue in the prostrate, brain, gall bladder, uterus, nerves, blood vessels and other regions of the body, including in systems that are not necessarily catheter-based.

System 10 may include a mapping catheter 14 and an ablation catheter 16. Each probe 14/16 may be separately introduced into target region 12 through a vein or artery (e.g., the femoral vein or artery) using a suitable percutaneous access technique. Alternatively, mapping catheter 14 and ablation catheter 16 can be assembled in an integrated structure for simultaneous introduction and deployment in target region 12.

Mapping catheter 14 may include a catheter shaft 18. The distal end of the catheter shaft 18 may include a three-dimensional multiple electrode structure 20. Structure 20 may take the form of a basket having a plurality of struts 22 (see FIG. 2), although other multiple electrode structures could be used. A plurality of mapping electrodes 24 (not explicitly shown on FIG. 1, but shown on FIG. 2) may be disposed along struts 22. Each electrode 24 may be configured to sense intrinsic physiological activity in the anatomical region. In some embodiments, electrodes 24 may be configured to detect activation signals of the intrinsic physiological activity within the anatomical structure (e.g., the activation times of cardiac activity).

Electrodes 24 may be electrically coupled to a processing system 32. A signal wire (not shown) may be electrically coupled to each electrode 24 on basket structure 20. The wires may extend through shaft 18 and electrically couple each electrode 24 to an input of processing system 32. Electrodes 24 may sense electrical activity in the anatomical region (e.g., myocardial tissue). The sensed activity (e.g., activation signals) may be processed by processing system 32, which may assist the physician by generating an electrical activity map (e.g., a vector field map, an activation time map, etc.) to identify the site or sites within the heart appropriate for a diagnostic and/or treatment procedure. For example, processing system 32 may identify a near-field signal component (e.g., activation signals originating from cellular tissue adjacent to the mapping electrode 24) or from an obstructive far-field signal component (e.g., activation signals originating from non-adjacent tissue). The near-field signal component may include activation signals originating from atrial myocardial tissue whereas the far-field signal component may include activation signals originating from ventricular myocardial tissue. The near-field activation signal component may be further analyzed to find the presence of a pathology and to determine a location suitable for ablation for treatment of the pathology (e.g., ablation therapy).

Processing system 32 may include dedicated circuitry (e.g., discrete logic elements and one or more microcontrollers; a memory or one or more memory units, application-specific integrated circuits (ASICs); and/or specially configured programmable devices, such as, for example, programmable logic devices (PLDs) or field programmable gate arrays (FPGAs)) for receiving and/or processing the acquired activation signals. In at least some embodiments, processing system 32 includes a general purpose microprocessor and/or a specialized microprocessor (e.g., a digital signal processor, or DSP, which may be optimized for processing activation signals) that executes instructions to receive, analyze and display information associated with the received activation signals. In such implementations, processing system 32 can include program instructions, which when executed, perform part of the signal processing. Program instructions can include, for example, firmware, microcode or application code that is executed by microprocessors or microcontrollers. The above-mentioned implementations are merely exemplary. A variety of processing systems 32 are contemplated.

In some embodiments, processing system 32 may be configured to measure the electrical activity in the myocardial tissue adjacent to electrodes 24. For example, in some embodiments, processing system 32 may be configured to detect electrical activity associated with a dominant rotor or divergent activation pattern in the anatomical feature being mapped. Dominant rotors and/or divergent activation patterns may have a role in the initiation and maintenance of atrial fibrillation, and ablation of the rotor path, rotor core, and/or divergent foci may be effective in terminating the atrial fibrillation. In either situation, processing system 32 processes the sensed activation signals to generate a display of relevant characteristics, such as an isochronal map, activation time map, action potential duration (APD) map, a vector field map, a contour map, a reliability map, an electrogram, a cardiac action potential, and/or the like. The relevant characteristics may be used by the physician to identify a site suitable for ablation therapy.

Ablation catheter 16 may include a flexible catheter body 34 that carries one or more ablation electrodes 36. Electrodes 36 may be electrically connected to a radio frequency (RF) generator 37 (or other suitable energy source) that is configured to deliver ablation energy to electrodes 36. Ablation catheter 16 may be movable with respect to the anatomical feature to be treated, as well as the structure 20. Ablation catheter 16 may be positionable between or adjacent to electrodes 24 of structure 20, for example, when the one or more ablation electrodes 36 are positioned adjacent to target region 12.

Processing system 32 may output data to a suitable output or display device 40, which may display relevant information for a clinician. Device 40 may be a CRT, LED, or other type of display, a printer, or the like. Device 40 may be utilized to present the relevant characteristics in a format most useful to the physician. In addition, processing system 32 may generate position-identifying output for display on device 40 that aids the physician in guiding ablation electrode(s) 36 into contact with tissue at the site identified for ablation.

Figure 2:
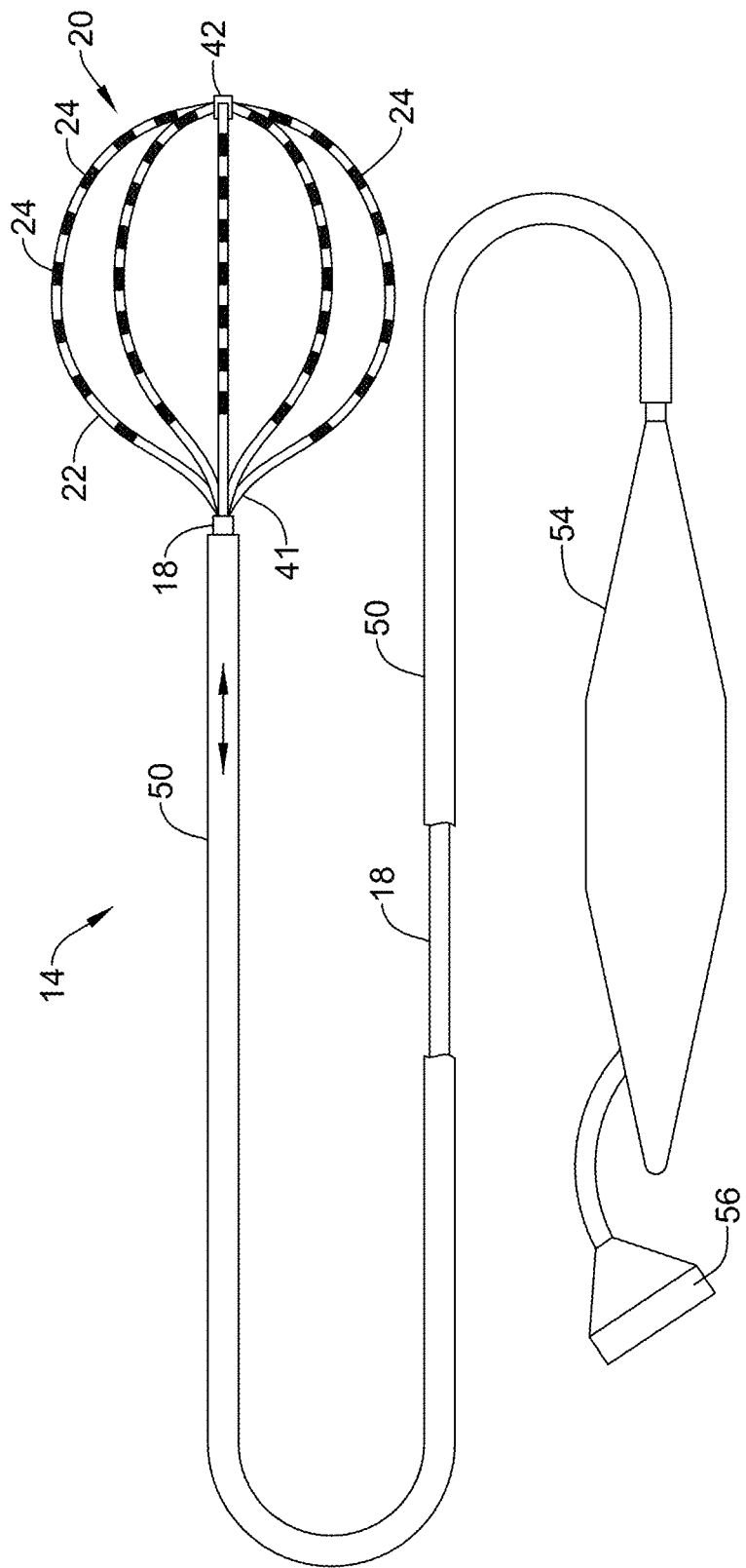
FIG. 2 is a side view of an example mapping catheter.

Turning now to FIG. 2, here some of the features of mapping catheter 14 can be seen. For example, FIG. 2 illustrates that structure 20 an end cap 42 between which struts 22 generally extend in a circumferentially spaced relationship. Struts 22 may be made of a resilient inert material, such as Nitinol, other metals, silicone rubber, suitable polymers, or the like and extend between a base region 41 and end cap 42 in a resilient, pretensioned condition, to bend and conform to the tissue surface they contact. In some embodiments, eight struts 22 may form structure 20. Additional or fewer struts 22 could be used in other embodiments. As illustrated, each strut 22 may carry eight mapping electrodes 24. Additional or fewer mapping electrodes 24 could be disposed on each strut 22 in other embodiments. Various dimensions are contemplated for structure. For example, structure 20 may be relatively small (e.g., 40 mm or less in diameter). In alternative embodiments, structure 20 may be smaller or larger (e.g., 40 mm in diameter or greater).

A slidable sheath 50 may be movable along the major axis of shaft 18. Moving sheath 50 distally relative to shaft 18 may cause sheath 50 to move over structure 20, thereby collapsing the structure 20 into a compact, low profile condition suitable for introduction into and/or removal from an interior space of an anatomical structure, such as, for example, the heart. In contrast, moving the sheath 50 proximally relative to shaft 18 may expose structure 20, allowing structure 20 to elastically expand and assume the basket configuration illustrated in FIG. 2.

A signal wire (not shown) may be electrically coupled to each mapping electrode 24. The wires may extend through shaft 18 of mapping catheter 20 (or otherwise through and/or along shaft 18) into a handle 54, in which they are coupled to an external connector 56, which may be a multiple pin connector. Connector 56 may electrically couple mapping electrodes 24 to processing system 32. These are just examples. Some addition details regarding these and other example mapping systems and methods for processing signals generated by the mapping catheter can be found in U.S. Pat. Nos. 6,070,094, 6,233,491, and 6,735,465, the disclosures of which are hereby expressly incorporated herein by reference.

Figure 3:
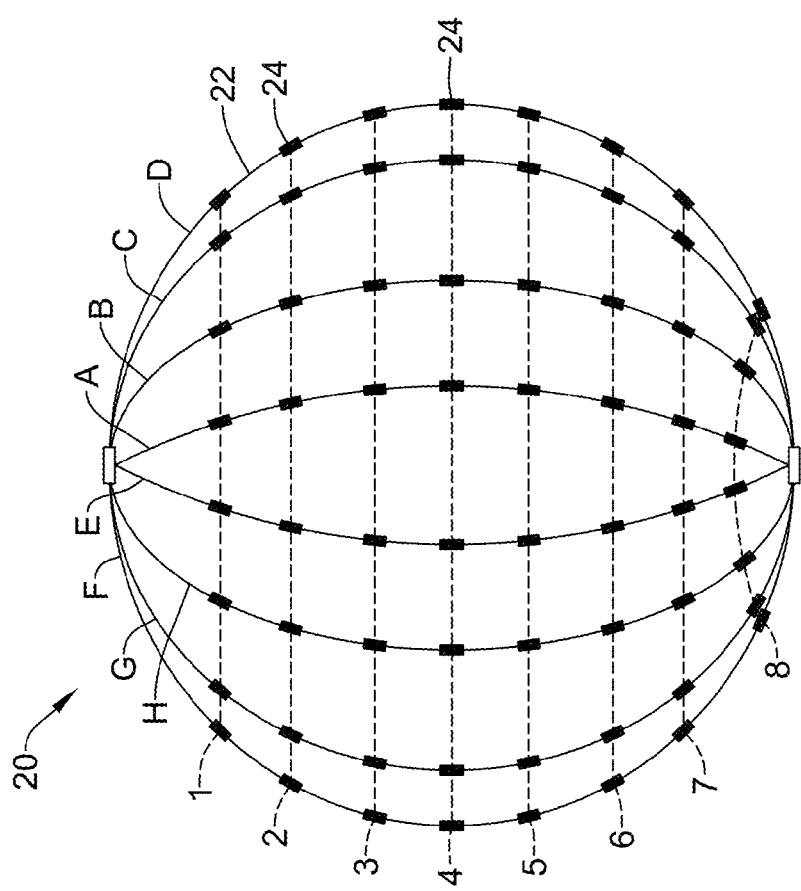
FIG. 3 is a schematic view of an example basket structure.

To illustrate the operation of the system 10, FIG. 3 is a schematic side view of basket structure 20. In the illustrated embodiment, basket structure includes 64 mapping electrodes 24. Electrodes 24 may be disposed in groups of eight electrodes (labeled 1, 2, 3, 4, 5, 6, 7, and 8) on each of eight struts 22 (labeled A, B, C, D, E, F, G, and H). While an arrangement of sixty-four mapping electrodes 24 is shown disposed on basket structure 20, mapping electrodes 24 may alternatively be arranged in different numbers (more or fewer splines and/or electrodes), on different structures, and/or in different positions. In addition, multiple basket structures can be deployed in the same or different anatomical structures to simultaneously obtain signals from different anatomical structures.

When basket structure 20 is positioned adjacent to the anatomical structure to be treated (e.g. left atrium, left ventricle, right atrium, or right ventricle of the heart), processing system 32 may be configured to record the activation signals from each electrode 24 channel related to physiological activity of the anatomical structure (e.g., the electrodes 24 measure electrical activation signals associated with the physiology of the anatomical structure). The activation signals of physiological activity may be sensed in response to intrinsic physiological activity or based on a predetermined pacing protocol instituted by at least one of the plurality of electrodes 24.

Electrodes 24 that contact healthy, responsive cellular tissue may sense a change in the voltage potential of a propagating cellular activation wavefront. Further, in a normal functioning heart, electrical discharge of the myocardial cells may occur in a systematic, linear fashion. Therefore, detection of non-linear propagation of the cellular excitation wavefront may be indicative of cellular firing in an abnormal fashion. For example, cellular firing in a rotating pattern may indicate the presence of dominant rotors and/or divergent activation patterns. Further, because the presence of the abnormal cellular firing may occur over localized target tissue regions, it is possible that electrical activity may change form, strength or direction when propagating around, within, among or adjacent to diseased or abnormal cellular tissue. Identification of these localized areas of diseased or abnormal tissue may provide a clinician with a location for which to perform a therapeutic and/or diagnostic procedure. For example, identification of an area including reentrant or rotor currents may be indicative of an area of diseased or abnormal cellular tissue. The diseased or abnormal cellular tissue may be targeted for an ablative procedure.

Figure 4:
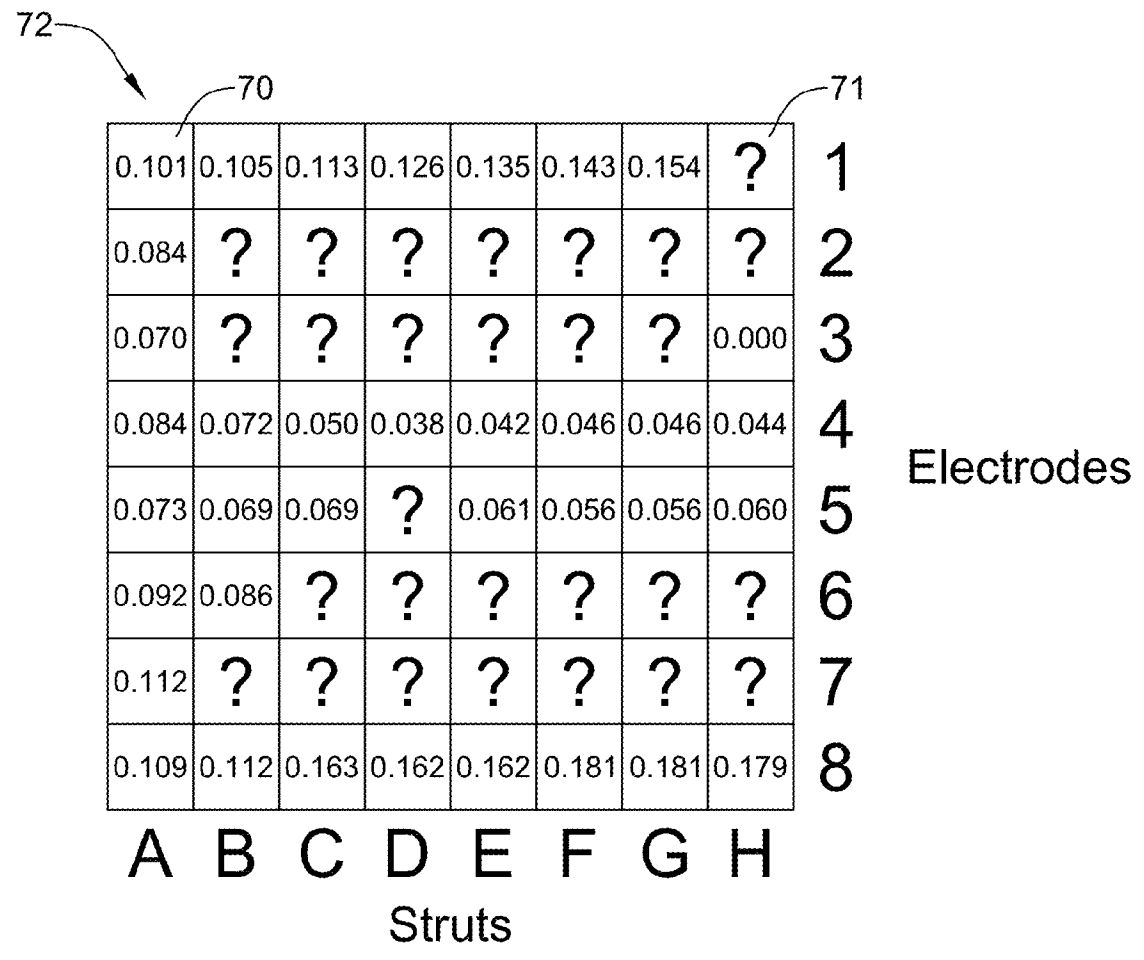

FIG. 4 illustrates an example activation map 72 showing activation times sensed by electrodes 24. Activation map 72 may include a two-dimensional grid that visually represents mapping electrodes 24. For example, activation map 72 may include an 8×8 matrix displaying sixty-four (64) electrode spaces that represent the sixty-four (64) electrodes on a constellation catheter or similar sensing device. Mapping electrodes 24 may be organized and/or identified by electrode number (e.g. electrodes 1-8) and spline location (e.g. splines A-H). Other combinations of electrodes and/or splines are contemplated.

The activation time for an electrode 24 may be defined as the time elapsed between an activation "event" being sensed on a target mapping electrode 24 and a reference electrode. For example, a space 70 on map 72 representing electrode 1 on strut A displays an activation time of 0.101 ms. However, it is possible that one or more electrodes 24 will be unable to sense and/or collect an activation time. For example, one or more spaces like a space 71 representing electrode 1 on spline H may display a "?." The "?" may indicate that the particular electrode corresponding to that location on the multiple electrode structure 20 cannot sense an activation time. Therefore, the "?" may represent missing signal data. Missing signal data and/or an incomplete activation map may prevent the identification of diseased or abnormal cellular tissue.

Some embodiments may include generating a color map corresponding to activation map 72. Each unique activation time may be assigned a unique, differentiating color. It is contemplated that a variety of color combinations may be included in generating the color-based activation time map. Further, the color map may be displayed on a display. Additionally, the color map may help a clinician identify the propagation direction of cellular firing. Activation map 72 may display an activation time or color for known signals and not display an activation time or color for unknown and/or missing activation time data. The use of color to differentiate activation times is just an example. It is contemplated that other means may be used to differentiate activation times. For example, texture, symbols, numbers, or the like may be used as differentiating characteristics.

In order to maximize the utility of activation map 72, it may be desirable to populate unknown activation times. Therefore, in some embodiments it may be desirable to interpolate activation times for missing signal data and populate and/or fill in the activation time map 72 accordingly. In practice, it may be that electrodes 24 in close proximity to one another will experience similar cellular events (e.g. depolarization). For example, as a cellular activation wavefront propagates across an atrial surface, electrodes 24 in close proximity to one another will likely experience similar cellular activation times. Therefore, when selecting an interpolation method, it may be desirable to select a method that incorporates the relative distance between neighboring electrodes and utilizes those distances in an algorithm to estimate unknown data points. One method to interpolate activation times and thereby fill in missing electrode data is to utilize an interpolation method that estimates the missing electrode data based on the electrode's relationship and/or proximity to known electrode data. The method may include identifying the physical position of all electrodes 24 in three-dimensional space, determining the distance between electrodes 24, and interpolating and/or estimating the missing electrode values. The estimated values may then be used to populate diagnostic displays (e.g. activation map). Therefore, the interpolation method may include any interpolation method that incorporates neighboring electrode information (e.g. distance between electrodes) in its estimation algorithm. Example interpolation methods may include Radial Basis Function (RBF) and/or Kriging interpolation. These are only examples. It is contemplated that other interpolation methods that incorporate neighboring data point information may be utilized with the embodiments disclosed herein.

As indicated above, some interpolation methods may incorporate the distance between electrodes as an input variable of their interpolation algorithm. For example, RBF and Kriging interpolation methods may incorporate the linear distance between unknown and known electrodes in their interpolation algorithms. The linear distance may be determined by calculating the "straight line" or "Euclidean" distance between electrodes 24. In non-curved space, it is generally understood that the shortest distance between two points is a straight line.

When collecting and analyzing the electrical activity of the heart, it may be desirable to collect and/or analyze the electrical activity as it is expressed and/or propagated through an anatomical region. It is generally understood that the anatomical shape of the interior walls of the heart are curved spaces. Further, because multiple electrode structure 20 may conform to the anatomical space in which it is deployed (e.g. heart chamber), electrodes 24 disposed on multiple electrode structure 20 may similarly conform to the anatomical space in which multiple electrode structure 20 is deployed. In practice, multiple electrode structure 20 is often deployed along the curved surface of an atrial chamber. In some embodiments it may be desirable to collect and/or analyze electrical activity as it occurs along the curved surface of an atrial chamber. Therefore, when incorporating the distance between electrodes into an interpolation method, it is often desirable to use the distance between the electrodes along the curved surface of the cardiac chamber. In contrast, it is often less desirable to calculate the linear distance between electrodes through open space and/or blood. Further, assuming a fixed distance between electrodes and/or using the linear distance of the "nearest neighboring electrode" may result in inaccurate and/or distorted results.

As stated, it may be desirable to substitute the curved distance between electrodes for the linear distance in some example interpolation methods. Geodesic distances may be understood to be the shortest distance between two points in curved space. Therefore, calculating the geodesic distance between two electrodes may better approximate the distance between the two electrodes in curved space. An example method for calculating the geodesic distance may include creating a coarse triangular mesh between electrodes 24. The coarse triangular mesh may then be upsampled. The upsampled mesh may then be utilized to calculate the shortest distance between electrodes. Once the shortest distance between electrodes 24 has been calculated, the geodesic distance between electrodes 24 may be calculated. After generating the geodesic distances between electrodes 24, the geodesic distances may be substituted for the linear distance between electrodes 24.

Figure 5:
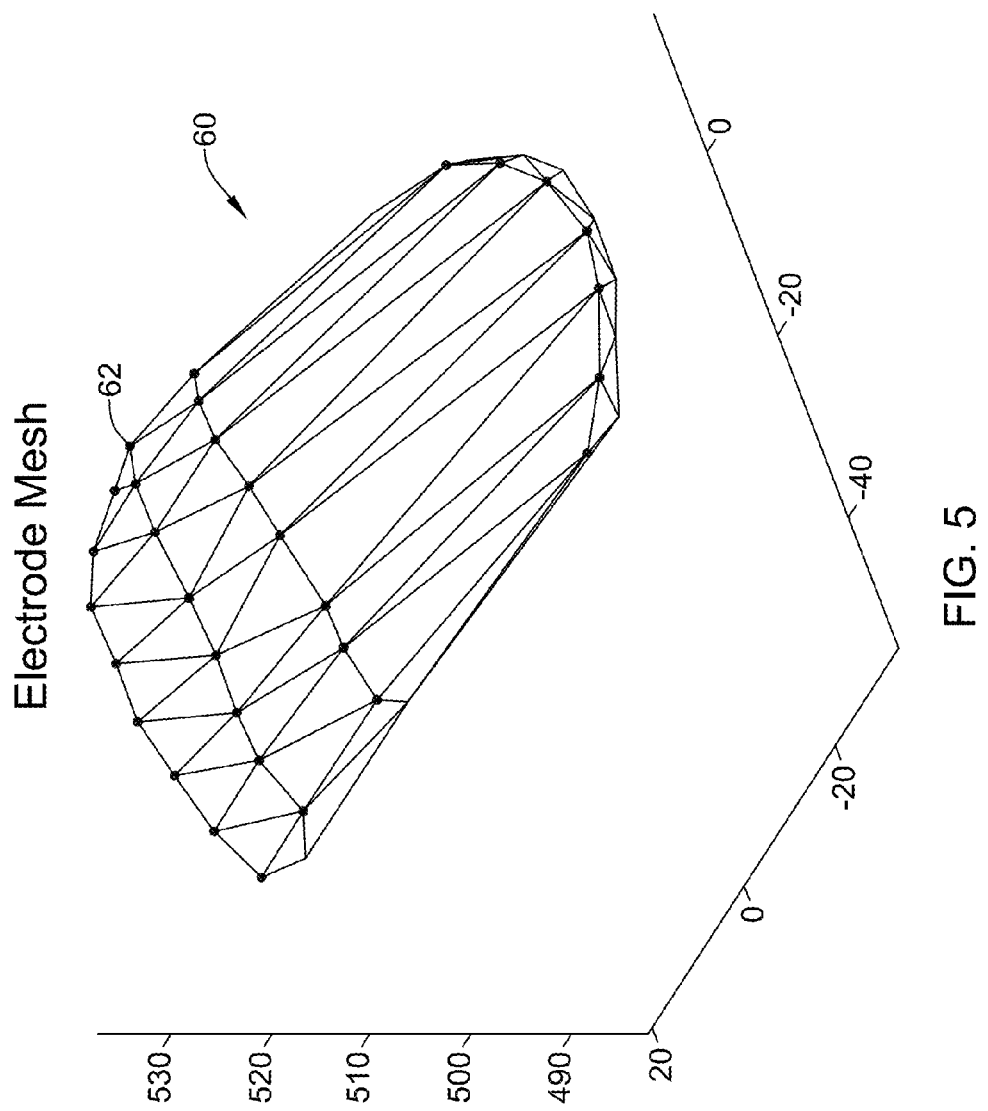
FIG. 5 is an illustration of an example electrode mesh.

FIG. 5 illustrates a mesh 60 representing the three-dimensional arrangement of mapping electrodes 24 deployed in a non-uniform or non-spherical configuration. The mesh 60 may include interconnected nodes and/or vertices 62. Vertices 62 may be disposed at locations where mapping electrodes 24 are positioned. In at least some embodiments, the mesh 60 may take the form of a course triangular mesh. Creating a course triangular mesh may include approximating the geometry and/or the shape of a three-dimensional structure such as the three dimensional arrangement of mapping electrodes 24. For example, a course triangular mesh may be designed to approximate the shape and physical relationships between electrodes 24 disposed on the basket structure 20 of a constellation catheter and/or similar sensing device deployed within a cardiac chamber of the heart. A triangular mesh may include a set of triangles that are drawn between the electrodes 24. Further, the three-dimensional configuration may include flat faces and straight edges and/or lines that connect electrodes 24 together by their common edges or corners. The corners of the triangular faces may be defined as vertices 62.

Figure 6:
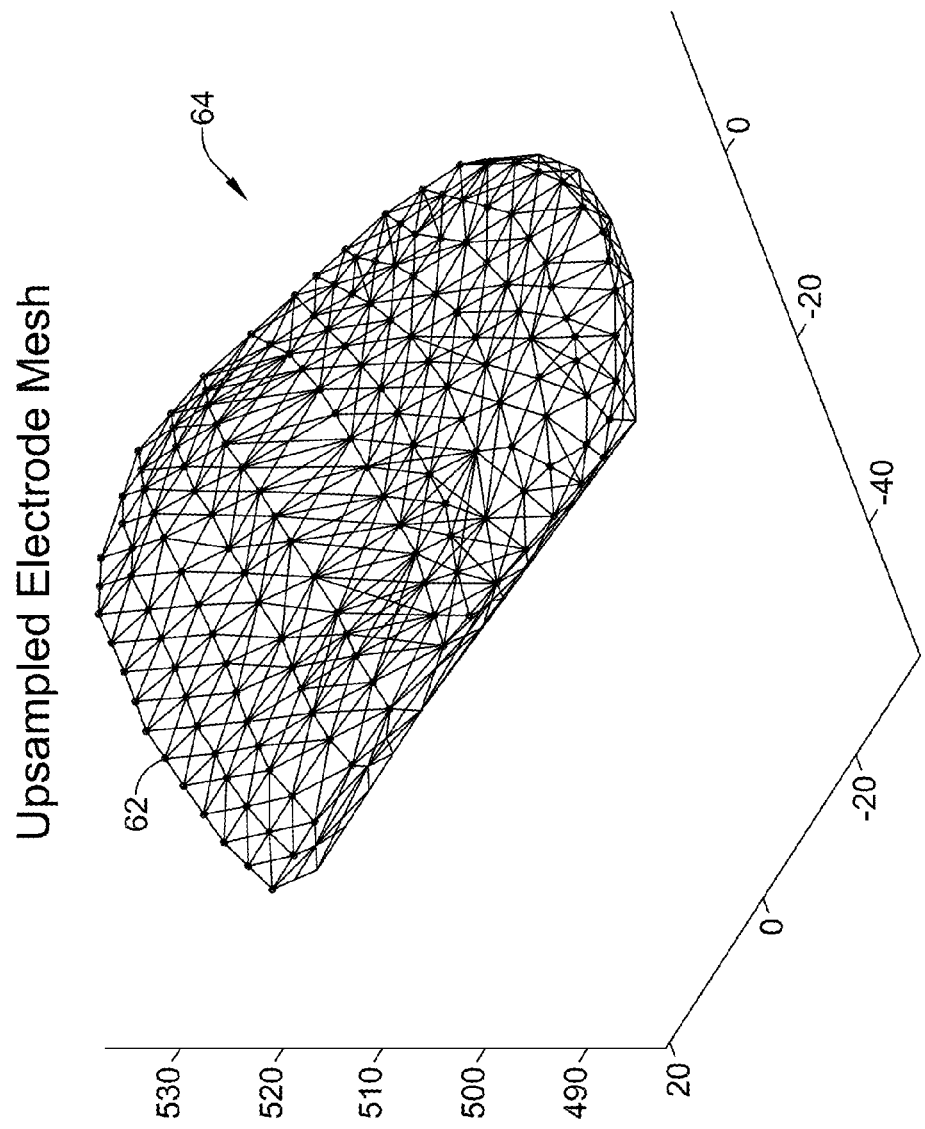
FIG. 6 is an illustration of an example upsampled electrode mesh.

In at least some embodiments, it may be desirable to further refine or "upsample" mesh 60. FIG. 6 illustrates a schematic upsampled mesh 64. The upsampled mesh 64 may include interconnected nodes and/or vertices 62. The upsampled mesh 64 may be generated from a course triangular mesh. Upsampling may include subdividing the triangles of the triangular mesh into additional triangles. The additional triangles may include flat faces and straight edges and/or straight lines connecting vertices 62 of the triangles.

The upsampled mesh 64 may be utilized to calculate the shortest distance between electrodes. For example, after the shortest distance between electrodes is calculated, the upsampled mesh 64 may be utilized to calculate the geodesic distances between electrodes. The geodesic distances may be substituted for the linear distance in an example interpolation method. For example, the geodesic distance between two electrodes may be substituted for the linear distance between the electrodes in RBF, Kriging or similar interpolation methods. Using geodesic distance estimations instead of linear distance approximations or assumptions may provide a more accurate estimate of the interpolated data points.

In at least some embodiments, one or more interpolation methods stated above may be incorporated, included, utilized, and/or integrated into processing system 32. Processing system 32 may be configured such that the interpolation method may be implemented to populate and/or fill in electrodes 24 having missing data on activation map 72. Further, processing system 32 may incorporate an "iterative" process to assess, populate and/or fill in electrodes 24 having missing data on activation map 72. The iterative process may cycle through determining an electrode 24 that has missing data, utilizing an interpolation method to estimate missing and/or inaccurate data and populating and/or filling in the missing data on the corresponding activation map 72. The processing system 32 may integrate and/or employ a feedback loop in the iterative process. For example, the processing system 32 may integrate and/or employ a feedback loop when interpolating, choosing, and/or assigning activation times and populating and/or filling in activation map 72. A feedback loop may be designed to permit an operator (e.g. physician, clinician) to select the number of iterations processing system 32 will implement to populate activation map 72. For example, a user (e.g. physician, clinician) may be able to input the number of iterations that processing system 32 will implement to populate activation map 72. It is further contemplated that processing system 32 may include a preset maximum number of iterations that it will implement when populating activation map 72.

The disclosed embodiments heretofore have focused on populating and/or estimating unknown and/or inaccurate data in an activation map. However, it is contemplated that the above methodologies may be utilized to estimate unknown and/or inaccurate data as it relates to any diagnostic display, data set, diagnostic visual representation, or the like. For example, the above methodologies may be utilized to estimate unknown and/or inaccurate data for a vector field map, isochronal map, or the like.

In at least some of the embodiments described above the disclosed methods assume analysis of sensed, collected, measured and transmitted electrical cellular data occurring during a single heartbeat and/or cardiac pulse. However, it is contemplated that any of the disclosed methods may be implemented across multiple beats or cardiac pacing time intervals. Further, data collected over multiple heartbeats may be analyzed using statistical methodologies and applied to the disclosed methods. For example, activation times may be collected over a series of heart beats and/or pulses. A statistical distribution of the collected activation times may be calculated, analyzed and incorporated into disclosed methods.

As described above, a variety of interpolation methods may be utilized to estimate missing or inaccurate data needed to populate and/or fill in diagnostic displays (e.g. an activation time map, vector field map, etc.). In general, interpolating inaccurate or missing data consists of inputting real-valued data (hereafter referred to as "known data" for simplicity) sensed by electrodes into an interpolation method, the output of which may be an estimated real value of the missing and/or inaccurate electrode data (hereafter referred to as "unknown data"). For purposes of this disclosure, it will be assumed that every electrode 24 may have a known three-dimensional position in space. Further, it may be assumed that up to 63 of 64 electrodes (i.e. all electrodes but the unknown electrode) may have a known data value. For example, for a constellation catheter or similar sensing device, 64 of the 64 electrodes present on basket structure 20 may have a known position in three-dimensional space and up to 63 of 64 may have a known data value. For example, electrodes 24 may sense local activation times, and therefore, 63 of the 64 electrodes may have known activation times which may be utilized by an interpolation method.

In practice, it may be that electrodes 24 in close proximity to one another will experience similar cellular events. For example, as a cellular activation wavefront propagates across an atrial surface, electrodes 24 in close proximity to one another will likely have similar cellular activation times. Therefore, when selecting an interpolation method, it may be desirable to select a method which incorporates the relative distance between neighboring electrodes and utilizes those distances in an algorithm to estimate unknown data points (e.g. estimate unknown activation times). Radial Basis Function (RBF) interpolation is an example methodology that uses relative distance between electrodes to analytically estimate the value of unknown data.

In some embodiments, it may be desirable to utilize a RBF as an interpolation methodology because, in general, its output values may depend on the relative distance of known values from the origin, or center of an unknown value. For purposes of this disclosure, the origin or center of an unknown value may correspond to unknown or missing electrode data. Therefore, a RBF may be utilized to interpolate unknown electrode data from surrounding, known electrode data. Further, the output of a RBF for each known electrode may be summed in order to incorporate the input of all known data points when interpolating an unknown data point. For example, a RBF may utilize the known data of up to 63 mapping electrodes when interpolating the value of an unknown data point. Example RBF's may include Gaussian, Multiquadric, Inverse Quadric and/or Polyharmonic Spline. These are only examples. It is contemplated that the methodology described herein may by applicable to any suitable RBF type.

In addition to incorporating the relative distance of neighboring electrodes into an interpolation method, it may also be desirable to "weigh" the contribution of those electrodes based on their distance from the unknown electrode. For example, it also may be desirable to "favor" the contribution of known data from electrodes close to an unknown electrode, and "penalize" or "limit" the contributions of known data from electrodes which are farther away from an unknown electrode. This preferential weighting of known electrode data may be performed by RBF interpolation though the incorporation of a "weighting coefficient."

For the purposes of this disclosure, weighting coefficients are statistically, mathematically and/or computationally derived values that are used to emphasize the contribution of one input parameter over another. For example, a known value (e.g. activation time) of a neighboring electrode in close proximity to an unknown value may be emphasized to a greater degree than a distant electrode when performing an interpolation methodology. Determining the weighting coefficients for a particular set of known input values may be generated by using a weighting "kernel." A weighting kernel may be a real-valued function used in statistical estimation techniques. The weighting kernel real-valued function may provide a given output value for a given input value. Example kernel functions may include uniform, triangular, tricube and Gaussian. These are just examples. It is contemplated that many different kernel functions may be utilized to generate weighting coefficients.

Figure 7:
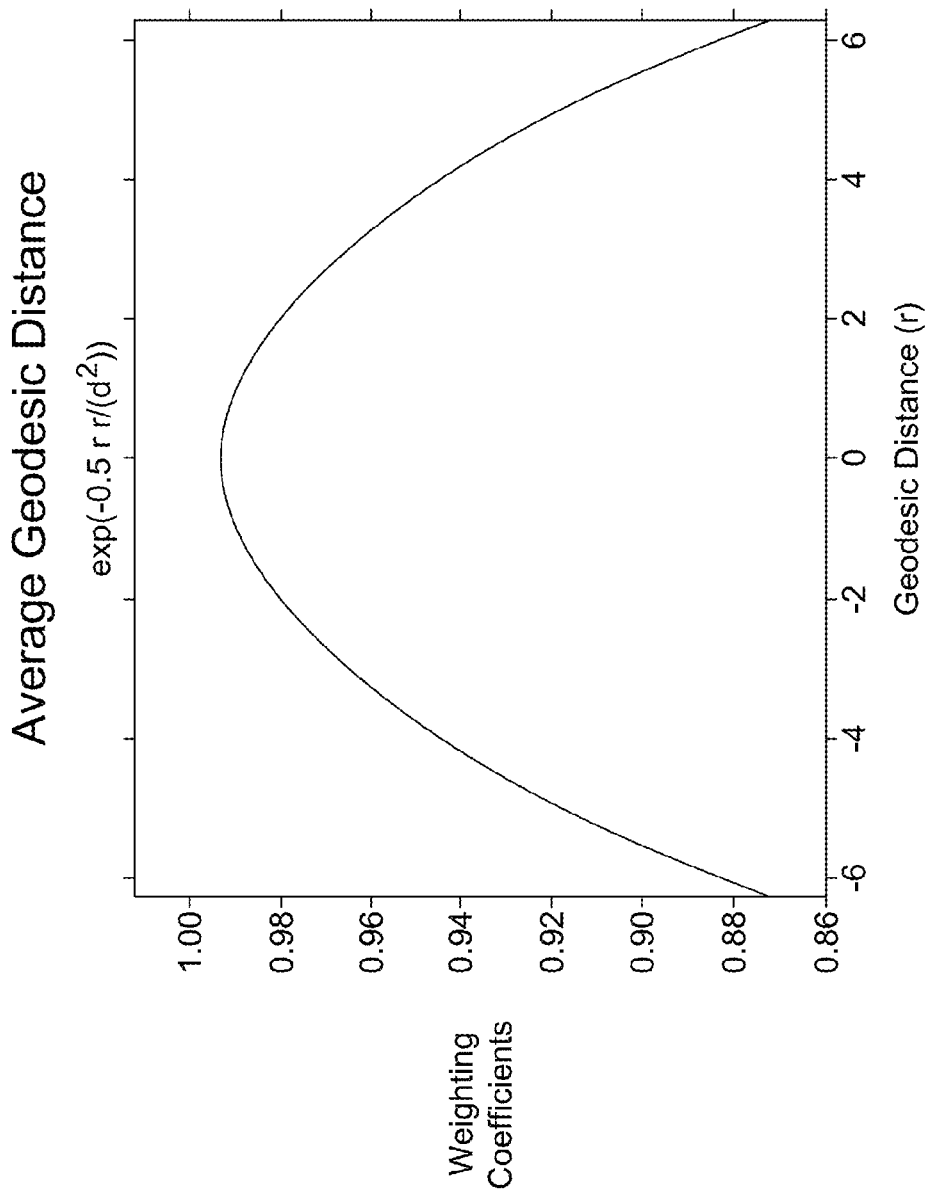
FIG. 7 is an illustration of an example weighting function.

As stated above, it is likely that electrodes 24 in close proximity to one another will experience similar cellular events. Therefore, it may be desirable to choose a weighting kernel that emphasizes, or favors, input data from neighboring electrodes and de-emphasizes input data from distant electrodes. Generating weighting coefficients that reflect this weighting scheme may be accomplished by utilizing a Gaussian kernel. FIG. 7 shows an example schematic Gaussian weighting kernel. The Gaussian kernel may be represented by the equation:

$$\text{Weighting Coefficient} = e^{(-0.5*r*r/(d^2))}; \text{ where}$$

r=geodesic distance from unknown data point to a known data point
d=average geodesic distance from unknown data point to all known data points As illustrated in FIG. 7, the input values for the Gaussian kernel is the geodesic distance from the unknown data point to a known data point. In this example, input values lie on the X-axis and may be labeled "geodesic distance." The center value "0" may represent the location of an unknown electrode. As indicated, values on the X-axis increase to the left and right of the center point "0." The increasing values may represent the geodesic distance of a known electrode from the center point of the unknown electrode. For example, a value of "2" may represent a geodesic distance of "2" units from the center of an unknown electrode to a known electrode. Geodesic distance is one example of an input variable contemplated by the embodiments disclosed herein. Other input values are contemplated for use with any of the methods disclosed herein.

Figure 8:
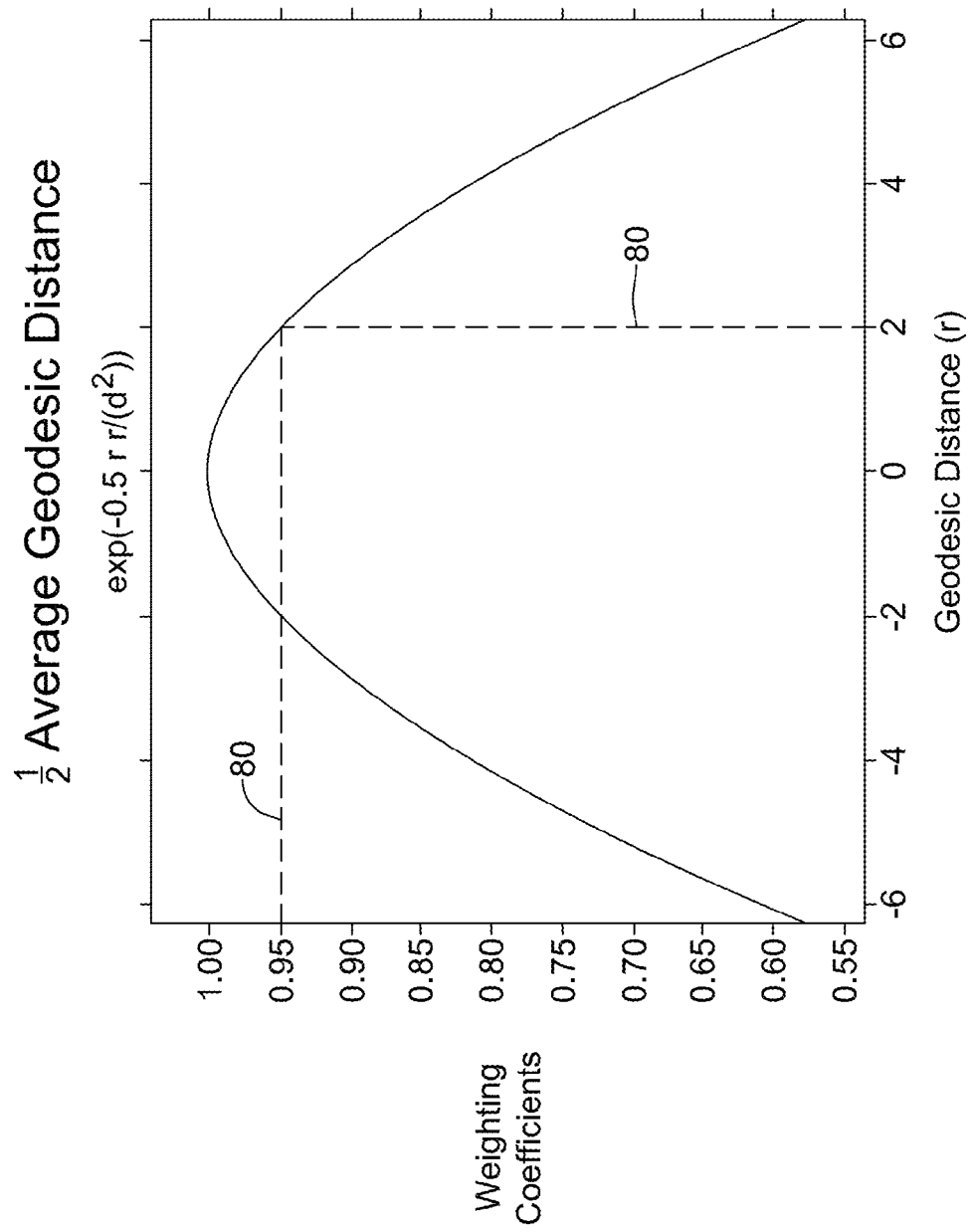
FIG. 8 is an illustration of an example conditioned weighting function.

In some embodiments it may be desirable to further "condition" the kernel to more accurately reflect the desired weighting of the input neighboring electrodes. Conditioning the kernel may include modifying the input variables of the kernel. For example, in the above weighting coefficient equation, the input variable "d" may represent the average geodesic distance from unknown data point to all known data points. Conditioning that kernel may include dividing the variable "d" in half. FIG. 8 illustrates a schematic "conditioned" Gaussian weighting kernel of FIG. 7. As illustrated in FIG. 8, the weighting coefficient scale is different as compared to FIG. 7. The "conditioned" Gaussian kernel may be represented by the equation:

$$\text{Weighting Coefficient} = e^{(-0.5 * r * r / (d/2)^2)};\text{ where}$$

r=geodesic distance from unknown data point to a known data point
d=average geodesic distance from unknown data point to all known data points As indicated above, the output value of the Gaussian kernel may be a weighting coefficient. For example, as illustrated by the dashed line 80 on FIG. 8, an input value of r=2 (e.g. r=geodesic distance) may represent an output value (i.e. weighting coefficient) of approximately 0.95. Weighting coefficients may be calculated for every known electrode. For example, weighting coefficients may be calculated for 63 of the 64 known electrode points mapped by a constellation catheter or similar sensing device. Further, the weighting coefficient may be incorporated into an interpolation methodology (e.g. RBF interpolation). The output of the interpolation methodology may provide that the estimation of an unknown electrode value based on a weighting and/or conditioned input of known electrode data.

While interpolation methods are useful and can provide a clinician with a reasonable approximation of unknown data, the confidence level of the interpolation may be unknown. Furthermore, the confidence of interpolated data may not be readily apparent or communicated to a clinician during an intervention. In other words, a clinician may not be aware of whether or not interpolated data is likely to be accurate when performing an intervention. The methods and devices disclosed herein are designed to help a clinician by determining and/or providing a confidence level for interpolated data.

In at least some instances, the confidence of interpolated data may be considered to be higher when the values for the interpolated data are based on data collected by electrodes positioned relatively close to electrodes with unknown data. As the distance between electrodes sensing/collecting unknown data and electrodes sensing/collecting known data increases, the confidence level may drop when interpolating the unknown data. Thus, the distance between electrodes may be one factor that may be used when assessing the confidence of interpolated data.

Figure 9:
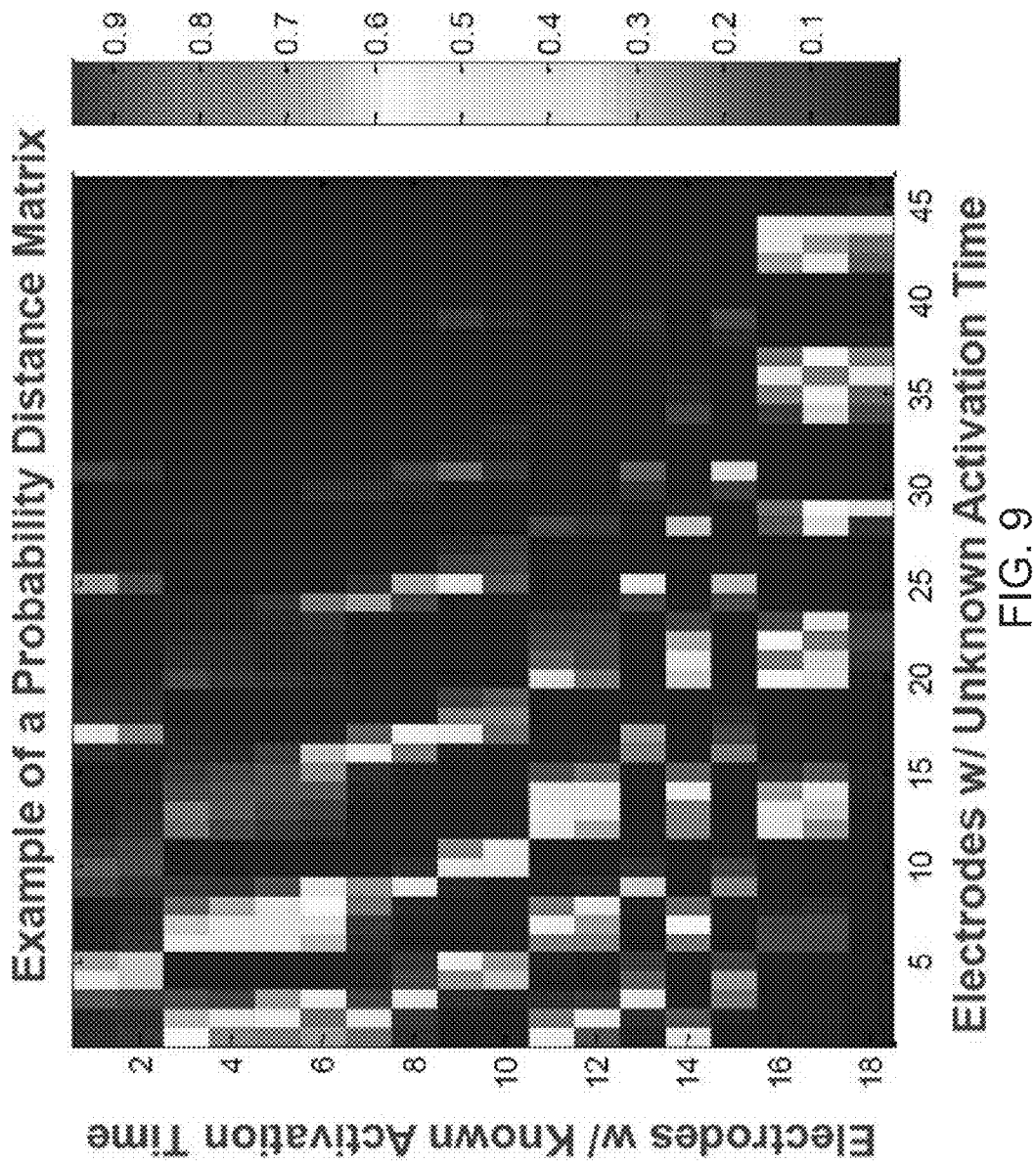
FIG. 9 illustrates an example probability distance matrix.

FIG. 9 illustrates an example probability distance matrix. The probability distance matrix may use distance between electrodes as the basis for the confidence of interpolated data. In this example, a number of electrodes that sense/collect known data (e.g., in this example the known data is used to determine a known activation time) are listed along the Y-axis and a number of electrodes with unknown data are listed along the X-axis. The activation times at electrodes with unknown data may be determined using an interpolation method such as those disclosed herein. When the interpolated values are determined using data from a number of electrodes that are positioned relatively close to the electrodes with unknown data, the confidence may be considered relatively high. Conversely, when the interpolated values are determined using data from a number of electrodes that are positioned further away from the electrodes with unknown data, the confidence may be considered lower. The probability matrix may be used to represent whether or not interpolated data based on electrodes with "known" data (e.g., activation times) is based on electrodes relatively close or relatively far away from the electrodes with "unknown" data. From this, the confidence level (e.g., the likelihood that that interpolated data is a good approximation for the actual activation time) for the interpolated data can be assessed and/or quantified.

It should be noted that FIG. 9 is shown schematically and in gray scale. The gray scale may make it challenging to convey all of the various gradations between the confidence levels. In practice, colors, patterns, numbers, or the like may be used to convey the confidence level in an efficient manner.

Figure 10:
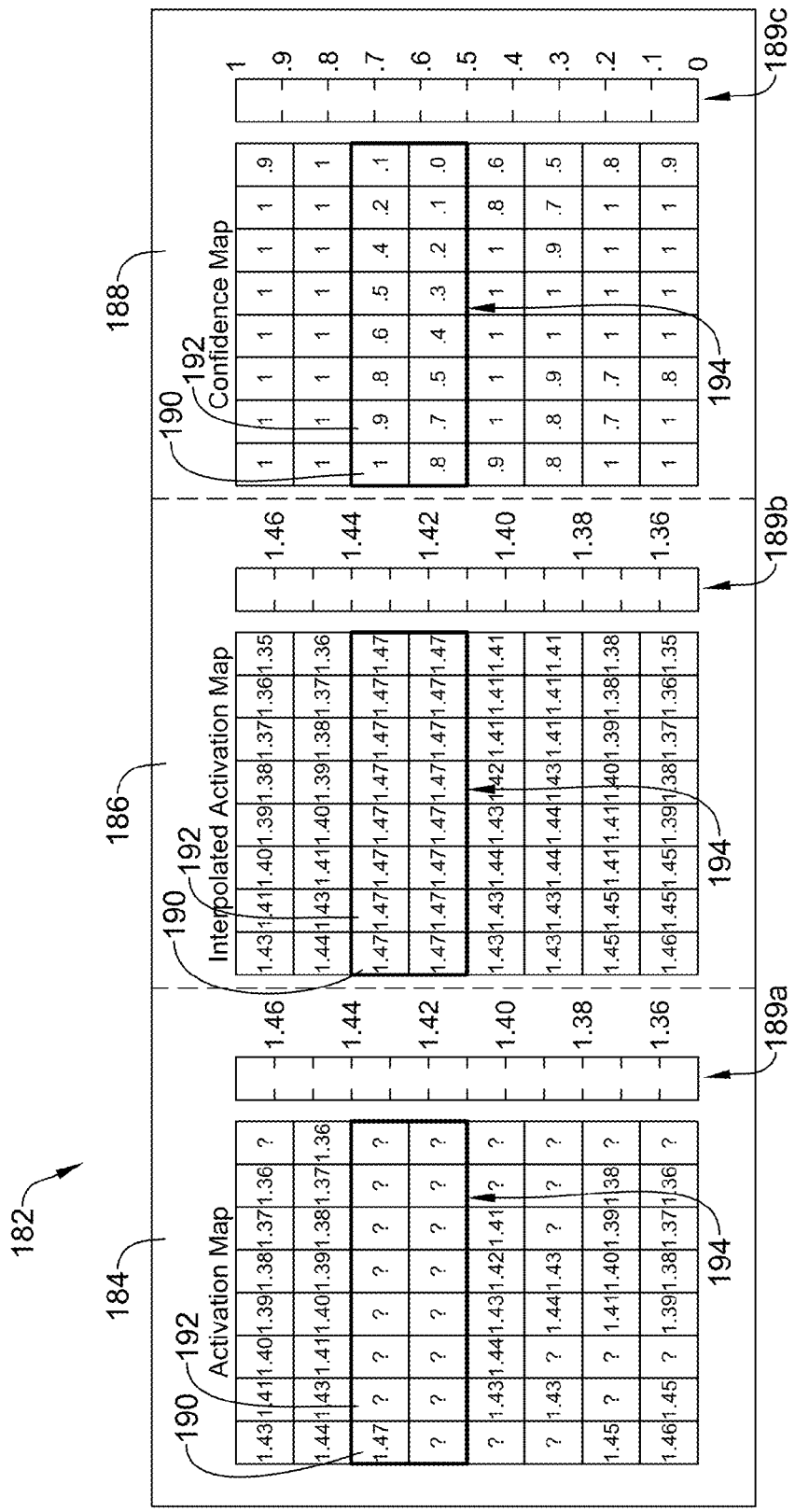
FIG. 10 illustrates an example display.

FIG. 10 illustrates an example graphical display 182 that utilizes confidence levels. Display 182 may include a plurality of panels such as a first panel 184, a second panel 186, and a third panel 188. In this example, first panel 184 may take the form of an activation map. The activation map may display activation times determined at electrodes 24. For example, a known activation time is shown in box 190 and a value is displayed in box 190 that represent the actual activation time. Another box 192 in the activation map displays a "?", which is meant to convey that the activation time is "unknown" for that particular electrode 24.

Second panel 186 may take the form of an interpolated activation map. In the interpolated activation map, an interpolation method such as those disclosed herein is utilized to determine activation times for the unknown data and the values are displayed in the interpolated activation map. For example, box 192, which displayed a "?" in the activation map in first panel 184, now displays a value representing an activation time in second panel 186.

In order to convey the confidence of the interpolated data, third panel 188 may take the form of a confidence map. Here, the confidence level of the interpolated data may be displayed. For example, a block of data 194 is highlighted with a bold outline in panels 184/186/188. The highlighting is provided for convenience and may or may not be utilized in display 182. In first panel 184, block 194 contains box 190 with a known activation time and additional boxes including box 192 with unknown activation times. In second panel 186, the known activation times are given a value using an interpolation method. Thus, within block 194, all the boxes include values representing activation times. In third panel 188, the confidence level of the interpolated data (as well as the "known" data is displayed. For example, the confidence level in box 190 is shown as "1". In other words, the confidence of the "known" data is considered to be 100% or 1. Other boxes with known activation times similarly show a confidence level of 1. The remaining boxes such as box 192 display a confidence level. For example, the confidence level in box 192 is shown as "0.9" or 90%. It can be seen that the confidence level of the various boxes with interpolated data within block 194 vary. In at least some embodiments, the confidence level is determined based on the distance between the electrode with unknown data and the electrode (s) with known data that were used to interpolate the unknown data. As the distance between the electrodes with known data increases from the electrodes with unknown data, the confidence level decreases. The confidence level may help a clinician to more efficiently assess, diagnose, and/or treat a patient.

It should be noted that FIG. 10 is shown schematically with numerical values and a corresponding numerical key (e.g., keys 189a/189b/189c). While the numerical values may be useful, in practice the data may utilize a color scheme, patterns, or the like to convey the information. As such, an appropriate key (e.g., a color-coded key) may be utilized. For example, panels 184/186/188 may include color-coded boxes and keys 189*a*/189*b*/189*c* may provide values that correspond to the various colors shown in panels 184/186/188.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device, comprising:
   a catheter shaft with a plurality of electrodes coupled thereto; and
   a processor coupled to the catheter shaft, wherein the processor is configured to: collect a set of signals from the plurality of electrodes, generate a data set from at least one of the set of signals, wherein the data set includes at least one known data point and one or more unknown data points, determine a distance between the at least one known data point and at least one of the one or more unknown data points, interpolate a value for an unknown data point of the one or more unknown data points using a weighted value of the at least one known data point, wherein the weighted value uses the determined distance, assign a confidence level to the interpolated value, and output to a display device the interpolated value and the assigned confidence level.

2. The medical device of claim 1, wherein the processing device is configured to determine activation times for the set of signals.

3. The medical device of claim 2, wherein the value for the unknown data point includes an activation time of the determined activation times for the unknown data point.

4. The medical device of claim 2, wherein, to determine an activation time of the activation times, the processing device is configured to: identify a fiducial point corresponding to a change in electrical potential and determine a time latency between a reference point and the fiducial point.

5. The medical device of claim 1, wherein to interpolate a value for an unknown data point of the one or more unknown data points, the processing device is configured to: create a mesh of interconnected nodes between the known data points, the unknown data points, or both the known and unknown data points.

6. The medical device of claim 5, wherein the processing device is further configured to upsample the mesh of interconnected nodes.

7. The medical device of claim 1, wherein the distance is a geodesic distance.

8. The medical device of claim 1, wherein the weighted value is determined from a weighting function.

9. The medical device of claim 1, wherein the processor is further configured to: generate a graphical display of at least one known data point, one or more unknown data points or both; and wherein the graphical display includes an activation map.

10. The medical device of claim 9, wherein the graphical display further comprises an interpolated activation map.

11. The medical device of claim 10, wherein the graphical display further comprises a confidence map representing the confidence level.

12. A method for displaying cardiac mapping data, the method comprising:
   determining a set of activation times from a set of signals sensed by electrodes coupled to a catheter shaft;
   storing the set of activation times on a memory, wherein the set of activation times includes one or more known activation times and one or more unknown activation times;
   outputting the set of activation times to a display unit;
   displaying the activation times on a first panel of the display unit;
   interpolating the unknown activation times;
   displaying the interpolated activation times on a second panel of the display unit;
   determining a respective level of confidence associated with each interpolated activation time;
   displaying a confidence map on a third panel of the display unit; and
   wherein the confidence map displays the determined respective levels of confidence for the interpolated activation times.

13. The method of claim 12, wherein storing a set of activation times on a memory includes identifying a fiducial point corresponding to a change in electrical potential and determining a time latency between a reference point and the fiducial point.

14. The method of claim 12, wherein interpolating the unknown activation times includes utilizing a non-linear distance between two electrodes of a constellation catheter.

15. The method of claim 12, wherein interpolating the unknown activation times includes utilizing a geodesic distance two electrodes of a constellation catheter.

16. The method of claim 12, wherein interpolating the unknown activation times includes weighting the known activation times and wherein weighting the known activation times includes determining weighting coefficients from a weighting function.

17. A medical device, comprising:
   a catheter shaft with a plurality of electrodes coupled thereto; and
   a processor coupled to the catheter shaft, wherein the processor is configured to: receive signals indicative of electrical activity sensed by a plurality of electrodes, determine activation times at the plurality of electrodes based on the sensed electrical activity, wherein the activation times include one or more known activation times and one or more unknown activation times, interpolate the one or more unknown activation times, determine a respective confidence level value for each interpolated activation time, assign the determined respective confidence levels to each of the interpolated activation times; and output the interpolated activation times and the determined respective confidence levels to a display device.

18. The medical device of claim 17, wherein the processor is further configured to: generate a graphical display; wherein the graphical display includes an activation map, an interpolated activation map, or both.

19. The medical device of claim 18, wherein the graphical display further comprises a confidence map representing the confidence level of the interpolated activation times.

* * * * *